(12) United States Patent
Vago et al.

(10) Patent No.: US 8,481,527 B2
(45) Date of Patent: Jul. 9, 2013

(54) BENZAMIDE DERIVATIVES AS BRADYKININ ANTAGONISTS

(75) Inventors: Istvan Vago, Budapest (HU); Gyula Beke, Budakeszi (HU); Eva Bozo, Budapest (HU); Sandor Farkas, Budapest (HU); Katalin Hornok, Budapest (HU); Gyorgy Keseru, Telki (HU); Eva Schmidt, Budapest (HU); Eva Szentirmay, Erd (HU); Monika Vastag, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 394 days.

(21) Appl. No.: 12/447,157

(22) PCT Filed: Oct. 27, 2007

(86) PCT No.: PCT/HU2007/000102
§ 371 (c)(1),
(2), (4) Date: Dec. 11, 2009

(87) PCT Pub. No.: WO2008/068540
PCT Pub. Date: Jun. 12, 2008

(65) Prior Publication Data
US 2010/0087423 A1      Apr. 8, 2010

(30) Foreign Application Priority Data
Oct. 27, 2006  (HU) ..................................... 0600808

(51) Int. Cl.
| C07D 207/08 | (2006.01) |
| C07D 211/18 | (2006.01) |
| C07D 211/44 | (2006.01) |
| C07D 211/22 | (2006.01) |
| C07D 211/58 | (2006.01) |
| C07D 211/26 | (2006.01) |
| C07D 211/62 | (2006.01) |
| C07D 207/26 | (2006.01) |
| C07D 211/34 | (2006.01) |
| C07D 211/68 | (2006.01) |
| A61K 31/18  | (2006.01) |
| A61P 29/00  | (2006.01) |

(52) U.S. Cl.
USPC ............... 514/217.11; 514/218; 514/235.8; 514/253.13; 514/254.02; 514/255.01; 540/575; 540/607; 544/121; 544/295; 544/360; 544/372; 544/391; 546/237

(58) Field of Classification Search
USPC ................ 514/217.11, 218, 235.8, 253.13, 514/254.02, 255.01; 540/575, 607; 544/121, 544/295, 360, 372, 391; 546/237
See application file for complete search history.

(56) References Cited

U.S. PATENT DOCUMENTS

| 5,714,497 A | 2/1998 | Christophe et al. |
| 6,017,961 A | 1/2000 | Flores et al. |
| 6,451,816 B1 | 9/2002 | Biedermann et al. |
| 6,538,008 B1 | 3/2003 | Boyce |
| 6,638,950 B2 | 10/2003 | Duncia et al. |
| 7,157,454 B2 | 1/2007 | Ferrari et al. |
| 7,393,873 B2 | 7/2008 | Anthony et al. |
| 8,034,827 B2 | 10/2011 | Beke et al. |
| 2004/0157886 A1 | 8/2004 | Domany et al. |
| 2007/0105902 A1 | 5/2007 | Lindsley et al. |
| 2010/0075978 A1 | 3/2010 | Bozo et al. |
| 2010/0105686 A1 | 4/2010 | Beke et al. |
| 2010/0298299 A1 | 11/2010 | Vago et al. |
| 2011/0190347 A1 | 8/2011 | Gage |
| 2011/0190348 A1 | 8/2011 | Banerjee |
| 2012/0295910 A1 | 11/2012 | Beke et al. |
| 2013/0029991 A1 | 1/2013 | Beke et al. |

FOREIGN PATENT DOCUMENTS

| GB | 1279843 | 6/1972 |
| WO | WO 00/75107 | 12/2000 |
| WO | WO 02/076964 | 10/2002 |
| WO | WO 02/099388 | 12/2002 |
| WO | WO 03/093245 | 11/2003 |
| WO | WO 2004/054584 | 7/2004 |
| WO | WO 2005/004810 | 1/2005 |

(Continued)

OTHER PUBLICATIONS

Burmistrov et al., "Some studies in the phenoxazine series," *Chemistry of Heterocyclic Compounds*, 1975, 11(12):1356-1358.

(Continued)

*Primary Examiner* — Bruck Kifle
(74) *Attorney, Agent, or Firm* — Fish & Richardson P.C.

(57) ABSTRACT

The present invention relates to new phenylsulfamoyl benzamide derivatives of formula (I)

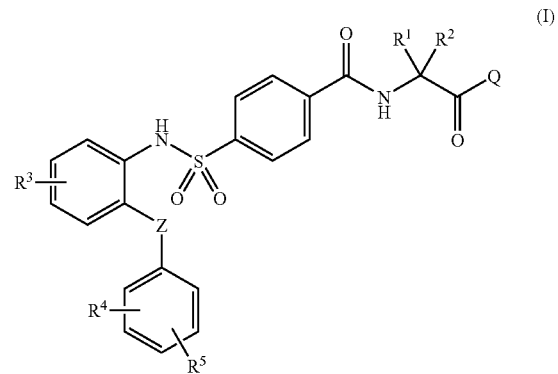

wherein
$R^1$-$R^5$ and Z are as defined in the claims, and optical antipodes or racemates and/or salts and/or hydrates and/or solvates thereof, which are selective antagonists of bradykinin B1, to processes for producing these compounds, to pharmacological compositions containing them and to their use in therapy or prevention of painful and inflammatory conditions.

14 Claims, No Drawings

FOREIGN PATENT DOCUMENTS

| WO | WO 2007/072092 | 6/2007 |
|----|----------------|--------|
| WO | WO 2009/111595 | 9/2009 |
| WO | WO 2011/094308 | 8/2011 |

OTHER PUBLICATIONS

Chem Abstr., 1976, 84 164313.
Chem Abstr., 1969, 70 68312.
Ferreira et al., "Evidence for the participation of kinins in Freund's adjuvant-induced inflammatory and nociceptive responses in kinin $B_1$ and $B_2$ receptor knockout mice," Neuropharmacology, 2001, 41(8):1006-1012.
Fox et al., "Antihyperalgesic activity of a novel nonpeptide bradykinin $B_1$ receptor antagonist in transgenic mice expressing the human $B_1$ receptor," Br J Pharmacol., 2005, 144(7):889-899.
Hamada and Tomita, "Chemotherapy of Drug II," Yakugaku Zasshi, 1968, 88(11):1361-1366 (English summary paragraph included).
Hess et al., "Cloning and pharmacological characterization of a human bradykin (BK-2) receptor," Biochem Biophys Res Commun., 1992, 184:260-268.
Ma and Heavens, "Basal expression of bradykinin $B_1$ receptor in the spinal cord in humans and rats," NeuroReport, 2001, 12(11):2311-2314.
Ma et al., "Basal expression of bradykinin $B_1$ receptor in peripheral sensory ganglia in the rat," NeuroReport, 2000, 11(18):4003-4005.
Ma, "The expression of bradykinin $B_1$ receptors on primary sensory neurones that give rise to small caliber sciatic nerve fibres in rats," Neuroscience, 2001, 107(4):665-673.
McEvoy et al., "2-Trifluoromethoxydibenz[b,e][1,4]diazepine and 2- trifluoromethoxydibenz[b,f][1,4]-oxazepine derivatives," J Med Chem., 1970, 13(2):295-297.
Menke et al., "Expression Cloning of a Human $B_1$ Bradykinin Receptor," J Biol Chem., 1994, 269(34):21583-21586.
Pesquero et al., "Hypoalgesia and altered inflammatory responses in mice lacking kinin B1 receptors," Proc Natl Acad Sci USA, 2000, 97(14):8140-8145.
Phagoo et al., "Autoregulation of Bradykinin Receptors: Agonists in the Presence of Interleukin-1β Shift the Repertoire of Receptor Subtypes from B2 to B1 in Human Lung Fibroblasts," Mol Pharmacol., 1999, 56:325-333.
Prado et al., "Mechanisms Regulating the Expression, Self-Maintenance and Signaling-Function of the Bradykinin B2 and B1 Receptors," J Cell Physiol., 2002, 193:275-286.
Schmutz et al., "Neue Synthese von Lactamen der Dibenz[v,f]-1, 4-thiazepin-, -oxazepin und Dibenz[b,e]-azepin-Reihe," Helvetica Chimica Acta, 1965, 48(38):336-347.
Synthesis, 1980, 677-688.
Wardrop et al., "Preparation of some dibenz[b,f][1,4]oxazepines and dibenz[b,e]azepines," J. Chem Soc, Perkin Trans 1, 1976, pp. 1279-1285.
Wood et al., "Benzodiazepines as Potent and Selective Bradykinin $B_1$ Antagonists," J Med Chem., 2003,46(10):1803-1woth806.
Wotherspoon and Winter, "Bradykinin B1 receptor is constitutively expressed in the rat sensory nervous system," Neuroscience Letters, 2000, 294(3):175-178.
Authorized Officer Russell English, PCT/HU2007/000102 International Search Report, mailed Apr. 7, 2008, 4 pages.
Authorized Officer Russell English, PCT/HU2007/000102 Written Opinion of the International Searching Authority, mailed Apr. 7, 2008, 5 pages.
Authorized Officer Beate Giffo-Schmitt, PCT/HU2007/000102 International Preliminary report on Patentability, issued Apr. 28, 2009, 5 pages.
Abdouh et al. "Retinal plasma extravasation in streptozotocin-diabetic rats mediated by kinin B (1) and B (2) receptors," Br. J. Pharmacol., 2008, 154:136-143.
Armstrong et al. "Pain-producing substance in human inflammatory exudates and plasma," J. Physiol., 1957, 135:350-370.
Babenko et al. "Experimental human muscle pain induced by intramuscular injections of bradykinin, serotonin, and substance," P. Eur, J. Pain, 1999, 3:93-102.

Bachvarov et al. "Cloning and pharmacological characterization of the rabbit bradykinin B2 receptor," J. Pharmacol. Exp. Ther., 1995, 275:1623-1630.
Bennett and Xie. "A peripheral mononeuropathy in rat that produces disorders of pain sensation like those seen in man," Pain, 1988, 33:87-107.
Bond et al. "Generation of kinins in synovial fluid from patients with arthropathy," Immunopharmacology, 1997, 36:209-216.
Bonica. "The need of a taxonomy," Pain, 1979, 6:247-248.
Campos et al. "Changes in paw oedema triggered via bradykinin B (1) and B (2) receptors in streptozotocin-diabetic rats," Eur. J. Pharmacol., 2001, 416:169-177.
Campos et al. "Expression and distribution of kinin B1 receptor in the rat brain and alterations induced by diabetes in the model of streptozotocin," Synapse, 2005, 57:29-37.
Cassim et al. "Kallikrein cascade and cytokines in inflamed joints," Pharmacol. Ther., 2002, 94:1-34.
Chopra et al. "Expression and function of bradykinin B1 and B2 receptors in normal and inflamed rat urinary bladder urothelium," J. Physiol., 2005, 562:859-871.
Christiansen et al. Up-regulation of functional kinin Bl receptors in allergic airway inflammation, J. Immunol., 2002, 169:2054-2060.
Cloutier et al. "Pharmacological characterization of the cardiovascular responses elicited by kinin B (1) and B (2) receptor agonists in the spinal cord of streptozotocin-diabetic rats," Br. J. Pharmacol., 2000, 130:375-385.
Costa et al. "Effect of novel selective non-peptide kinin B (1) receptor antagonists on mouse pleurisy induced by carrageenan," Peptides, 2006, 27:2967-2975.
Cruwys et al. "The role of bradykinin B1 receptors in the maintenance of intra-articular plasma extravasation in chronic antigen-induced arthritis," Br. J. Pharmacol., 1994, 113:940-944.
Davis and Perkins. "The involvement of bradykinin B1 and B2 receptor mechanisms in cytokine-induced mechanical hyperalgesia in the rat," Br .J. Pharmacol., 1994, 113:63-68.
Dlamini and Bhoola. "Upregulation of tissue kallikrein, kinin B1 receptor, and kinin B2 receptor in mast and giant cells infiltrating oesophageal squamous cell carcinoma," J. Clin. Pathol., 2005, 58:915-922.
Eggerickx et al. "Molecular cloning, functional expression and pharmacological characterization of a human bradykinin B2 receptor gene," Biochem, Biophys. Res. Commun., 1992, 187:1306-1313.
Eisen. "Plasma kinins in synovial exudates," Br. J. Exp. Pathol., 1970, 51:322-327.
Eisenbarth et al. "Sensitization to bradykinin B1 and B2 receptor activation in UV-B irradiated human skin," Pain, 2004, 110:197-204.
Erdos. "Some old and some new ideas on kinin metabolism," J. Cardiovasc. Pharmacol., 1990, 15-Suppl 6:LS20-S24.
Ferreira et al. "Reduced nerve injury-induced neuropathic pain in kinin B1 receptor knock-out mice," J. Neurosci., 2005, 25:2405-2412.
Fox et al. "Regulation and function of spinal and peripheral neuronal B1 bradykinin receptors in inflammatory mechanical hyperalgesia," Pain., 2003, 104:683-691.
Gabra et al. "The kinin system mediates hyperalgesia through the inducible bradykinin B1 receptor subtype: evidence in various experimental animal models of type 1 and type 2 diabetic neuropathy," Biol. Chem., 2006, 387:127-143.
Gabra et al. "Absence of diabetic hyperalgesia in bradykinin Bl receptor-knockout mice," Regul. Pept., 2005, 127:245-248.
Gabra et al. "Role of bradykinin B (1) receptors in diabetes-induce hyperalgesia in streptozotocin-treated mice," Eur. J. Pharmacol., 2002, 457:115-124.
Gabra et al. "Beneficial effect of chronic treatment with the selective bradykinin B1 receptor antagonists, R-715 and R-954, in attenuating streptozotocin-diabetic thermal hyperalgesia in mice," Peptides, 2003, 24:1131-1139.
Gabra et al. "Hyperalgesia in non-obese diabetic (NOD) mice: a role for the inducible bradykinin B1 receptor," Eur. J. Pharmacol., 2005, 514:61-67.

Galizzi et al. "Up-regulation of [3H]-des-Arg10-kallidin binding to the bradykinin B1 receptor by interleukin-1 beta in isolated smooth muscle cells: correlation with B1 agonist-induced PGI2 production," *Br. J. Pharmacol.*, 1994, 113:389-394.

Gama et al. "Modulation of allergic and immune complex-induced lung inflammation by bradykinin receptor antagonists," *Inflamm. Res.*, 2004, 53:78-83.

Goldstein and Wall. "Activation of protein formation and cell division by bradykinin and des-Arg9-bradykinin," *J.Biol.Chem.*, 1984, 259:9263-9268.

Gougat et al. SSR240612 [(2R)-2-[((3R)-3-(1,3-benzodioxol-5-yl)-3-[[(6-methoxy-2-naphthyl)sulfonyl]amino]propanoyl)amino]-3-(4-[[2R,6S)-2,6-dimethylpiperidinyl]methyl]phenyl)-N-isopropyl-N-methylpropanamide hydrochloride], a new nonpeptide antagonist of the bradykinin B1 receptor: biochemical and pharmacological characterization, *J. Pharmacol. Exp. Ther.*, 2004, 309:661-669.

Hara et al. "The relevance of kinin B1 receptor upregulation in a mouse model of colitis," *Br. J. Pharmacol.*, 2008, 154:1276-1286.

Huang et al. "Contribution of bradykinin B(1) and B(2) receptors in allergen-induced bronchial hyperresponsiveness," *Am. J. Respir. Crit Care Med.*, 1999, 160:1717-1723.

Julius and Basbaum. "Molecular mechanisms of nociception," *Nature*, 2001, 413:203-210.

Kim and Chung. "An experimental model for peripheral neuropathy produced by segmental spinal nerve ligation in the rat," *Pain*, 1992, 50:355-363.

Klein et al. "Blockade of the kinin B1 receptor ameliorates glomerulonephritis," *J. Am. Soc. Nephrol.*, 2010, 21:1157-1164.

Klein et al. "Delayed blockade of the kinin B1 receptor reduces renal inflammation and fibrosis in obstructive nephropathy," *FASEB J.*, 2009, 23:134-142.

Koyama et al. "Bradykinin stimulates lung fibroblasts to release neutrophil and monocyte chemotactic activity," *Am. J. Respir. Cell Mol. Biol.*, 2000, 22:75-84.

Lawson et al. "Enhanced dermal and retinal vascular permeability in streptozotocininduced type 1 diabetes in Wistar rats: blockade with a selective bradykinin B1 receptor Antagonist," *Regul. Pept.*, 2005a, 124:221-224.

Lawson et al. "Effects of a selective bradykinin B1 receptor antagonist on increased plasma extravasation in streptozotocin-induced diabetic rats: distinct vasculopathic profile of major key organs," *Eur. J. Pharmacol.*, 2005b, 514:69-78.

Levy and Zochodne. "Increased mRNA expression of the B1 and B2 bradykinin receptors and antinociceptive effects of their antagonists in an animal model of neuropathic pain," *Pain*, 2000, 86:265-271.

MacNeil et al. "Cloning and pharmacological characterization of a rabbit bradykinin B1 receptor," *Biochim. Biophys. Acta.*, 1995, 1264:223-228.

Mage et al. "Induction of B1 receptors in streptozotocin diabetic rats: possible involvement in the control of hyperglycemia-induced glomerular Erk 1 and 2 phosphorylation," *Can. J. Physiol Pharmacol.*, 2002, 80:328-333.

Marceau et al. "The B1 receptors for kinins," *Pharmacol. Rev.*, 1998, 50:357-386.

Marceau and Regoli. "Therapeutic options in inflammatory bowel disease:experimental evidence of a beneficial effect of kinin B1 receptor blockade," *Br. J. Pharmacol.*, 2008, 154:1163-1165.

Marin-Castano et al. "Differential induction of functional B1-bradykinin receptors along the rat nephron in endotoxin induced inflammation," *Kidney Int.*, 1998, 54:1888-1898.

Mathis et al. "B1 and B2 kinin receptors mediate distinct patterns of intracellular Ca2+ signaling in single cultured vascular smooth muscle cells," *Mol. Pharmacol.*, 1996, 50:128-139.

McEachern et al. "Expression cloning of a rat B2 bradykinin Receptor," *Proc. Natl. Acad. Sci. U.S.A.*, 1991, 88:7724-7728.

Meini et al. "The longitudinal muscle of rat ileum as a sensitive monoreceptor assay for bradykinin B1 receptors," *Br. J. Pharmacol.*, 1996, 117:1619-1624.

Melmon et al. The presence of a kinin in inflammatory synovial effusion from arthritides of varying etiologies, *Arthritis Rheum.*, 1967, 10:13-20.

Moreau et al. "The kallikrein-kinin system: current and future pharmacological targets," *J. Pharmacol. Sci.*, 2005, 99:6-38.

Nadar et al. "Immunoreactive B1 receptors in human transbronchial tissue," *Immunopharmacology.*, 1996, 33:317-320.

Ni et al. Molecular cloning and expression of rat bradykinin B1 receptor, *Biochim. Biophys. Acta.*, 1998, 1442: 177-185.

Nickel. "Interstitial cystitis: characterization and management of an enigmatic urologic syndrome," *Rev. Urol.*, 2002, 4:112-121.

Nsa et al. "Antagonists for kinin B1 and B2 receptors in the mouse," *Can. J. Physiol Pharmacol.*, 1997, 75:558-562.

Ongali et al. "Expression of kinin B1 receptors in the spinal cord of streptozotocindiabetic rat," *Neuroreport.*, 2004, 15:2463-2466.

Perkins et al. "Antinociceptive activity of the bradykinin B1 and B2 receptor antagonists, des-Arg9, [Leu8]-BK and HOE 140, in two models of persistent hyperalgesia in the rat," *Pain.*, 1993, 53:191-197.

Porreca et al. Antinociceptive pharmacology of N-[[4-(4,5-dihydro-1H-imidazol-2-yl)phenyl]methyl]-2-[2-[[ (4-methoxy-2,6-d imethylphenyl) sulfonyl]methylamino]ethoxy]-N-methylacetamide, fumarate (LF22-0542), a novel nonpeptidic bradykinin B1 receptor antagonist, *J. Pharmacol. Exp. Ther.*, 2006, 318:195-205.

Prat et al. "Bradykinin B1 receptor expression and function on T lymphocytes in active multiple sclerosis," *Neurology*, 1999, 53: 2087-2092.

Pruneau et al. "Targeting the kallikreinkinin system as a new therapeutic approach to diabetic retinopathy," *Curr. Opin. Investig. Drugs*, 2010, 11:507-514.

Rashid et al. Switching of bradykininmediated nociception following partial sciatic nerve injury in mice. *J. Pharmacol. Exp. Ther.*, 2004, 308:1158-1164.

Regoli and Barabe. "Pharmacology of bradykinin and related kinins,"*Pharmacol. Rev.*, 1980, 32:1-46.

Regoli et al. "Receptors for bradykinin in rabbit aortae," *Can. J. Physiol Pharmacol.*, 1977, 55:855-867.

Sato et al. "Bradykinin stimulates alveolar macrophages to release neutrophil, monocyte, and eosinophil chemotactic activity," *J. Immunol.*, 1996, 157:3122-3129.

Schanstra et al. "Bradykinin B(1) receptor-mediated changes in renal hemodynamics during endotoxin-induced inflammation," *J. Am. Soc. Nephrol.*, 2000, 11:1208-1215.

Seltzer et al. "A novel behavioral model of neuropathic pain disorders produced in rats by partial sciatic nerve injury," *Pain*, 1990, 43:205-218.

Sevcik et al. "Analgesic efficacy of bradykinin B1 antagonists in a murine bone cancer pain model," *J. Pain.*, 2005, 6:771-775.

Stadnicki et al. "Immunolocalization and expression of kinin B1R and B2R receptors in human inflammatory bowel disease," *Am. J. Physiol Gastrointest. Liver Physiol.*, 2005, 289:G361-G366.

Tiffany and Burch. "Bradykinin stimulates tumor necrosis factor and interleukin-1 release from macrophages," *FEBS Lett.*, 1989, 247:189-192.

Vianna et al. "Up-regulation of kinin B1 receptor in the lung of streptozotocin-diabetic rat: autoradiographic and functional evidence," *Br. J. Pharmacol.*, 2003, 138:13-22.

Wang et al. "Expression and cellular localization of tissue kallikrein-kinin system in human adrenal gland," *Am. J. Physiol.*, 1996, 271:F709-F716.

Wantuch et al. "Pharmacological validation of a model of cystitis pain in the mouse," *Neurosci. Lett.*, 2007, 421-250-252.

Werner et al. "Peripheral kinin B(1) and B(2) receptor-operated mechanisms are implicated in neuropathic nociception induced by spinal nerve ligation in rats," *Neuropharmacology.*, 2007, 53:48-57.

Westermann et al. "Gene deletion of the kinin receptor B1 attenuates cardiac inflammation and fibrosis during the development of experimental diabetic cardiomyopathy," *Diabetes.*, 2009, 58:1373-1381.

Whalley et al. "The effect of kinin agonists and antagonists on the pain response of the human blister base," *NaunynSchmiedebergs Arch. Pharmacol.*, 1987, 336:652-655.

Yamaguchi-Sase et al. "Amelioration of hyperalgesia by kinin receptor antagonists or kininogen deficiency in chronic constriction nerve injury in rats," *Inflamm. Res.*, 2003, 52:164-169.

Babenko et al. "Experimental human muscle pain induced by intramuscular injections of bradykinin, serotonin, and substance," *P. Eur. J. Pain*, 1999, 3:93-102.

Christiansen et al. Up-regulation of functional kinin B1 receptors in allergic airway inflammation, *J. Immunol.*, 2002, 169:2054-2060.

Apelt et al., "Development of a New Class of Nonimidazole Histamine H3 Receptor Ligands with Combined Inhibitory Histamine N-Methyltransferase Activity," *J. Med. Chem.*, 2002, 45:1128-1141.

Behr et al., "Synthesis of Alicyclic Diamines," *J. Am. Chem. Soc.*, Jul. 1946, 68(7):1296-1297.

Bergbreiter et al., "Soluble Polymer-Supported Catalysts Containing Azo Dyes," *Org. Lett.*, 2002, 4(5):737-740.

Bergeron and McManis, "Total synthesis of (.+−.)-15-deoxyspergualin," *J. Org. Chem.*, May 1987, 52(9):1700-1703.

Bonica. "The need of a taxonomy," *Pain*, 1979, 6:247-252.

Boulton, "Management of Diabetic Peripheral Neuropathy," *Clin. Diabetes*, 23(1): 9-15, 2005.

Chemical Abstracts Service Database Accession No. 2021940186 & Enamine Screening Library, Jan. 17, 2008, Enamine, Kieve, Ukraine, 1 page.

Chemical Abstracts Service Database Accession No. 852687-99-1, 2005, 1 page.

Dener et al., "Monocharged inhibitors of mast cell tryptase derived from potent and selective dibasic inhibitors," *Bioorg Med Chem Lett.* 11(17):2325-2330, 2001.

Dodart et al., "Immunization reverses memory deficits without reducing brain A burden in Alzheimer's disease model," *Nat. Neurosci.*, 5(5): 452-457, 2002.

Ennaceur and Delacour, "A new one-trial test for neurobiological studies of memory in rats. 1: Behavioral data," *Behav. Brain Res.*, 31(1), 47-59, 1988.

Golinske et al., "Electrocarboxylation of chlorinated aromatic compounds," *Collect. Czech. Chem. Commun.*, 2000, 65(9):862-880.

Halfpenny et al., "Highly selective .kappa.-opioid analgesics. 3. Synthesis and structure-activity relationships of novel N-[2-(1-pyrrolidinyl)-4- or -5-substituted cyclohexyl]arylacetamide derivatives," *J. Med. Chem.*, 1990, 33(1):286-291.

Hamada et al., "Synthesis and antifungal activity of 2-chloro-4-amino-5-(p-halophenoxy)phenyl thiocyanate compounds," *Chemical Abstracts* vol.67, No. 15 (1967) 73282m, p. 6888.

Hamada et al., "Synthesis and Antifungal Activity of 2-Chloro-4-amino-5-(p-halogenophenoxy) phenylthiocyanate Compounds. I," *Yakugaku Zasshi*, 1967, 87(5):591-596.

Holden, "Global Survey Examines Impact of Depression," *Science*, 288(5463): 39-40, 2000.

Itoh et al., "Synthesis and pharmacological evaluation of carboxamide derivatives as selective serotoninergic 5-HT(4) receptor agonists," *Eur. J. Med. Chem.*, 1999, 34:329-341.

Jung et al., "Synthesis and biological evaluation of novel T-type Ca2+ channel blockers," *Bioorganic & Medicinal Chemistry*, 2004, 12(15):3965-3970.

Khwaja et al., "Current and Emerging Therapies for Painful Diabetic Neuropathies," *Journal, Indian Academy of Clinical Medicine*, 2007, vol. 8, No. 1, Summary, p. 55, col. 1, para 3-5.

Leeb-Lundberg et al., "International Union of Pharmacology. XLV. Classification of the Kinin Receptor Family: from Molecular Mechanisms to Pathophysiological Consequences," *Pharmacol Rev.*, 2005, 57:27-77.

Matsuo et al, "New 2-Aryliminoimidazolidines I. Synthesis and Antihypertensive Properties of 2-(2-Phenoxyphenylimino) imadazolidines and Related Compounds," *Chemical and Pharmaceutical Bulletin* (1985) 33(10): 4409-4421.

McCombie et al., "The bromination of 2-nitro- and 2-acetamido-diphenyl ether," *J. Chem. Soc.*, 1930, 1202-1208.

Menzel et al., "Process Development of a Potent Bradykinin 1 Antagonist," *Organic Process Research & Development*, 2009, 13:519-524.

Mitaš et al., "Substituent Effect on Acidity of Substituted 2-(4-Nitrobenzoylamino)alkanamides in Methanol-Dimethyl Sulfoxide Mixtures," *Collect. Czech. Chem. Commun.*, 1998, 63:85-93.

Moore et al., "Antiinflammatory fluoroalkanesulfonanilides. 3. Other fluoroalkanesulfonamido diaryl systems," *J. Med. Chem.*, 1975, 18(4):386-391.

Nsa Allogho et al., "Antagonists for kinin B1 and B2 receptors in the mouse," *Can J Physiol Pharmacol.*, 1997, 75(6):558-562.

Ogino et al., "Muscarinic $M_3$ receptor antagonists with (2R)-2-[(1R)-3,3-Difluorocyclopentyl]-2-hydroxyphenylacetamide Structures. Part 2," *Bioorganic & Medicinal Chemistry Letters*, 2003, 13(13):2167-2172.

Okubo et al., "Design, synthesis and structure-affinity relationships of aryloxyanilide derivatives as novel peripheral benzodiazepine receptor ligands," *Bioorg. Med. Chem.*, 2004, 12:423-438.

Otsuka et al., "Syntheses of Peptides Related to the N-Terminal Structure of Corticotropin. IV. The Synthesis of the Amino Acid Sequences, Lys-Pro-Val-Gly and Lys-Pro-Val-Gly-Lys," *Bull. Chem. Soc. Jpn.*, 1964, 37(10):1471-1477.

Patino et al., "Modelling, synthesis and biological evaluation of an ethidium-arginine conjugate linked to a ribonuclease mimic directed against TAR RNA of HIV-1," *Eur J Med Chem.*, 2002, 37(7):573-584.

Perrone et al., "N-[2-[4-(4-Chlorophenyl)piperazin-1-yl]ethyl]-3-methoxybenzamide: A Potent and Selective Dopamine D4 Ligand," *J. Med. Chem.*, 1998, 41(24):4903-4909.

Prat et al., "Kinin B1 Receptor Expression on Multiple Sclerosis Mononuclear Cells," *Arch Neurol.*, 2005, 62:795-800.

Seddon, "Pseudopolymorph: A Polemic," *Crystal Growth & Design*, 4(6):1087-1087, (2004).

Singer and Andrews, "Mutagenicity and chemistry of N-nitroso-N-(parasubstituted-benzyl)methylamines," *J. Med. Chem.*, Mar. 1983, 26(3):309-312.

Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," *J Med Chem.*, 2000, 43(9):1878-1885.

Uhlmann and Pfleiderer, "Nucleotide. XIV. Substituierteβ-Phenyläthyl-Gruppen. Neue Schutzgruppen für Oligonucleotid-Synthesen nach dem Phosphorsäuretriester-Verfahren," [XIV. Substituted β-Phenyl-ethyl Groups. New Blocking Groups for Oligonucleotide Syntheses by the Phosphotriester Approach] *Helv. Chim. Acta*, 1981, 64(5):1688-1703.

Vaucher et al., "Object Recognition Memory and Cholinergic Parameters in Mice Expressing Human Presenilin 1 Transgenes," *Exp. Neurol.* 175(2), 398-406, 2002.

Regnier et al; Bronchodilator substances. Part 1: synthesis and structure-activity relationships between new benzoic and heterocyclic amide derivatives; Arzneimittelforschung; Dec. 1974; 24(12):1964-1970.

BENZAMIDE DERIVATIVES AS BRADYKININ ANTAGONISTS

CROSS-REFERENCE TO RELATED APPLICATIONS

This application is a National Stage application under 35 U.S.C. §371 and claims benefit under 35 U.S.C. §119(a) of International Application No. PCT/HU2007/000102 having an International Filing Date of Oct. 27, 2006, which claims the benefit of priority of HU P06 00808 having a filing date of Oct. 27, 2006.

FIELD OF THE INVENTION

The present invention relates to new phenylsulfamoyl benzamide derivatives of formula (I) and optical antipodes or racemates and/or salts and/or hydrates and/or solvates thereof which are useful in the treatment or prevention of painful and inflammatory processes. The present invention also relates to the processes for producing compounds of formula (I) and to pharmacological compositions containing the same.

BACKGROUND OF THE INVENTION

Kinins are endogenous peptides formed in plasma and peripheral tissues in response to tissue injury or infection following catalytic cleavage of kininogens by kallikrein enzymes. Kinins play an important role in the pathophysiological processes accompanying pain and inflammation. Their biological actions are mediated by two G-protein coupled membrane receptors, denoted B1 and B2. Both B1 and B2 receptors have been cloned [*Biochem. Biophys. Res. Commun.*, 184 (1992) 260-268 and *J. Biol. Chem.*, 269 (1994) 21583-21586] and the mechanisms regulating their expression, self-maintenance and signalling function is under intensive investigations [*Mol. Pharmacol.*, 56 (1999) 325-333 and *J. Cell. Physiol.* 193 (2002) 275-286].

The first set of kinins, bradykinin (BK) and kallidin (LysBK) preferentially act through stimulation of constitutively expressed and rapidly desensitising B2 receptors, which are widely distributed in many tissues. On the other hand, their active carboxypeptidase metabolites, the second set of kinins, desArg$^9$BK (DABK) and LysdesArg$^9$BK (LysDABK) activate inducible and non-desensitising B1 receptors, which are rarely expressed under non-pathological conditions. Generally B1 receptors rapidly appear after injuries of various natures (tissue trauma, infections, etc.). Thus the B1 receptor up-regulation appears to be part of a generalized response that includes the local co-expression (eventually up-regulation) of enzymes, receptors, autacoids, cytokines and chemokines that notoriously play key roles in the early and late responses of tissues to various types of injury.

In animal models it has been demonstrated that there is a switch in dominance of function from B2 to B1 in chronic inflammatory states. While the B2 receptor is implicated in the acute phase of the inflammatory and pain response, the B1 receptor is involved in the chronic phase of this response. The involvement of kinin receptors in inflammation and pain transduction has been supported by the results of studies on mice lacking bradykinin B1 receptors. B1 receptor deficient mice are different from wild-type mice in sensory functions, exhibiting increased analgesic thresholds to noxious chemical and heat stimuli, and drastic reduction in the accumulation of polymorphonuclear leukocytes at sites of inflammation [*PNAS*, 97 (2000) 8140-8145 and *Neuropharmacology* 41 (2001) 1006-1012]. Furthermore the most original finding in B1 receptor deficient mice was the direct evidence for a role of central kinin receptors in nociception suggesting that the hypoalgesia seen in B1-receptor knockout mice is partly due to reduced central sensitisation in the spinal cord. However, apart from the above changes B1 knockout mice were apparently normal without any apparent pathological changes.

Apart from the evidence of basal expression of B1 receptors on the periphery recently more and more evidence shows that B1 receptors are constitutively expressed 'centrally' in some neuronal elements, including the spinal cord and some higher structures as well. The function of these receptors is unclear but they have been implicated in pain transmission and hyperalgesia. Therefore, B1 receptor antagonists are believed to be useful in alleviating pain not only via peripheral sites but also to have possibly broader spectrum of analgesic effects if they block central B1 receptors as well [*NeuroReport* 11 (2000) 4003-4005; *NeuroReport*, 12 (2001) 2311-2313; *Neuroscience* 107 (2001) 665-673 and *Neuroscience Letters* 294 (2000) 175-178].

On the basis of scientific data bradykinin receptors are involved in mediation of pain and hyperalgesia in several ways. B1 receptor antagonists may have diverse modes of action. They have (1) indirect ('peripheral') effects on the nociceptors via inhibition of release of other algogenic mediators. N.B. B1 receptors appear upon inflammatory induction on cells adjacent to sensory neurones (macrophages, fibroblasts or endothelial cells) are involved in releasing mediators (prostaglandins, cytokines and nitric oxide) that sensitize or activate the nociceptors. (2) direct ('peripheral') effects on nociceptors expressing B1 receptors (constitutively) or upon induction and (3) 'central' effects on pain processing in the superficial dorsal horn of spinal cord.

Therefore, an orally active non-peptide bradykinin B1 receptor antagonist could be a potential therapeutic agent in the treatment of chronic inflammatory pain.

Several patents and patent applications describe bradykinin B1 receptor antagonists which have different chemical structures. Such documents are for instance the following international patent applications: WO200075107, WO02076964, WO04054584, WO02099388, WO05004810.

SUMMARY OF THE INVENTION

We have found a class of benzamide derivatives which have high affinity for bradykinin B1 receptors and selectivity over bradykinin B2 receptors. The selectivity is particularly important as the undesired side effects of the compounds are much less pronounced.

The present invention relates to new phenylsulfamoyl benzamide derivatives of formula (I)

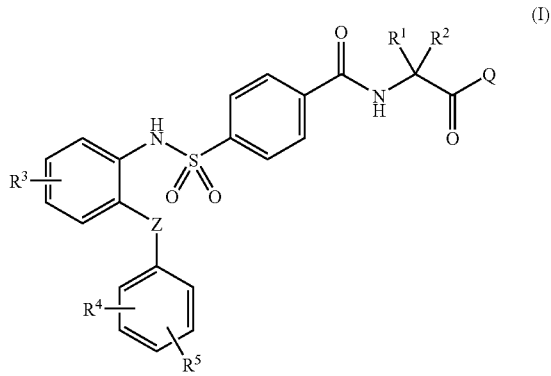

wherein
R$^1$ is hydrogen atom or C$_1$-C$_4$ alkyl group;
R$^2$ is selected from (1) hydrogen atom; (2) C$_1$-C$_6$ straight or branched alkyl group; (3) —(CH$_2$)$_n$—NH$_2$; (4) —(CH$_2$)$_n$—OH; (5) —(CH$_2$)$_n$—CO—NH$_2$; (6) —(CH$_2$)$_n$—CO- OR$^c$; (7) benzyl optionally substituted with one or more hydroxy group or halogen atom; or R$^1$, R$^2$ and the carbon atom to which they are both attached together form a 3-7 membered cycloalkyl ring;

R$^3$, R$^4$ and R$^5$ are independently of each other hydrogen atom; halogen atom; cyano; nitro; amino; or amino substituted with one or more C$_1$-C$_4$ alkyl group; trifluoromethyl; C$_1$-C$_4$ alkyl; C$_1$-C$_4$ alkoxy; trifluoromethoxy; C$_1$-C$_4$ alkoxycarbonyl; —C(=O)—NH$_2$ or hydroxy group;

Z is selected from (1) single bond; (2) oxygen atom; (3) CH$_2$ group; (4) CO group; (5) NR$^c$ group; (6) S atom; (7) SO$_2$ group;

Q is selected from

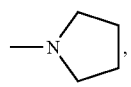
(1)

optionally substituted with —(CH$_2$)$_m$—OH group, or —(CH$_2$)$_n$—X—P group;

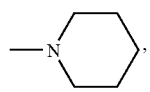
(2)

optionally substituted with one or more C$_1$-C$_4$ alkyl group, one or more halogen atom, —(CH$_2$)$_m$—OH group, —(CH$_2$)$_m$—NH$_2$ group, —(CH$_2$)$_m$—CO—NH$_2$ group, trifluoromethyl group, oxo group, —(CH$_2$)$_m$—CN group; —NH—CO—(C$_1$-C$_4$ alkyl) group, —NH—SO$_2$—(C$_1$-C$_4$ alkyl) group, —(CH$_2$)$_m$—COOR$^c$ group, CO—NR$^c$R$^d$ group, —(C$_1$-C$_4$ alkoxy) group, —NH—CO—(CH$_2$)$_m$—CF$_3$ group, —NH—SO$_2$—CH$_2$—CF$_3$ group;

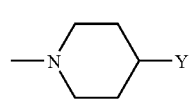
(3)

group;

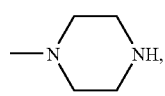
(4)

optionally substituted with oxo group, —SO$_2$—(C$_1$-C$_4$ alkyl) group, C$_1$-C$_4$ alkyl group, —CO—(C$_1$-C$_4$ alkyl) group, —(CH$_2$)$_m$—O—(CH$_2$)$_m$—OH group, —(CH$_2$)$_m$—OH group, —SO$_2$—NR$^c$R$^d$ group, —CO—NR$^c$R$^d$ group;

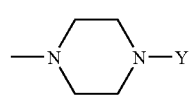
(5)

group;

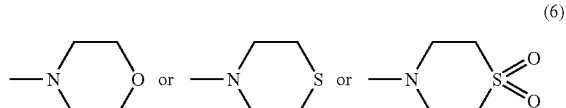
(6)

group;

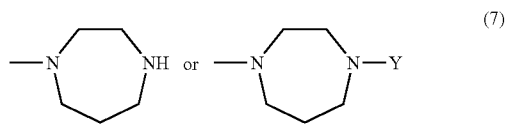
(7)

group;

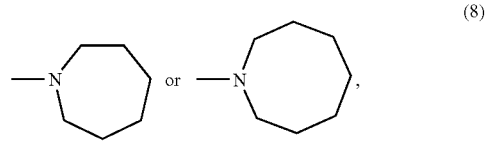
(8)

optionally substituted with —(CH$_2$)$_m$—OH group;

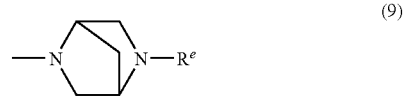
(9)

group;

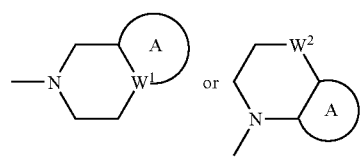
(10)

group;

(11)

group;

Y is selected from (1) —(CH$_2$)$_n$—NR$^a$R$^b$; (2) —(CH$_2$)$_n$—X—P group;

n is an integer from 0 to 6;

m is an integer from 0 to 3;

X is selected from (1) single bond; (2) oxygen atom; (3) —CO—NR$^c$ group; (4) CO or SO$_2$ group;

P is selected from (1) phenyl group, optionally substituted with one or more halogen atom, hydroxy, cyano, amino or C$_1$-C$_4$ alkyl group; (2) a saturated, partially unsaturated or aromatic 4-7 membered ring containing 1-3 heteroatom selected from O, S, SO$_2$ and N; wherein said ring is optionally substituted with one or more halogen atom, oxo, hydroxy, cyano, amino or C$_1$-C$_4$ alkyl group; (3) C$_5$-C$_8$ cycloalkyl group;

R$^a$ and R$^b$ are (1) hydrogen atom, with the proviso that R$^a$ and R$^b$ can not be simultaneously hydrogen atom; (2) straight or branched C$_1$-C$_6$ alkyl group; (3) R$^a$, R$^b$ and the nitrogen atom to which they are both attached together form a saturated, partially unsaturated or aromatic 4-7 membered ring containing 0-3 heteroatom (in addition to the nitrogen atom to which R$^a$ and R$^b$ attached) selected from O, S, SO$_2$ and N; wherein said ring is optionally substituted with one or more halogen atom, oxo, cyano, hydroxy or C$_1$-C$_4$ alkyl group;

$R^c$ is hydrogen atom or $C_1$-$C_4$ alkyl group;
$R^d$ is hydrogen atom, $C_1$-$C_4$ alkyl group, $C_1$-$C_4$ hydroxyalkyl group, $C_3$-$C_8$ cycloalkyl group;
$R^e$ is hydrogen atom, $C_1$-$C_4$ alkyl group, benzyl group;
A is (1) a $C_4$-$C_7$ cycloalkyl ring; (2) a saturated, partially unsaturated or aromatic 5-7 membered ring containing 0-4 heteroatom including $W^1$ selected from O, S, $SO_2$ and N; wherein said ring is optionally substituted with one or more halogen atom, oxo, cyano, hydroxy, amino, phenyl or $C_1$-$C_4$ alkyl group;
B is a saturated, partially unsaturated or aromatic 4-7 membered ring containing 1-3 heteroatom selected from O, S, $SO_2$ and N; wherein said ring is optionally substituted with one or more halogen atom, oxo, cyano, hydroxy, amino, phenyl or $C_1$-$C_4$ alkyl group;
$W^1$ is carbon atom, nitrogen atom, or CH group;
$W^2$ is oxygen atom, sulfur atom, NH, $CH_2$ or $SO_2$ group;
and optical antipodes or racemates and/or salts and/or hydrates and/or solvates thereof.

The invention also relates to the pharmaceutical compositions containing the compounds of formula (I) or optical antipodes or racemates or salts or hydrates or solvates thereof as active ingredient.

Furthermore objects of the present invention are the synthesis of compounds of formula (I), and the chemical and pharmaceutical manufacture of medicaments containing these compounds, as well as the methods of treatment with these compounds, which means administering to a mammal to be treated—including human—effective amount/amounts of compounds of formula (I) of the present invention as such or as medicament.

DETAILED DESCRIPTION OF THE INVENTION

The present invention relates to new bradykinin B1 receptor antagonist phenylsulfamoyl benzamide derivatives of formula (I)

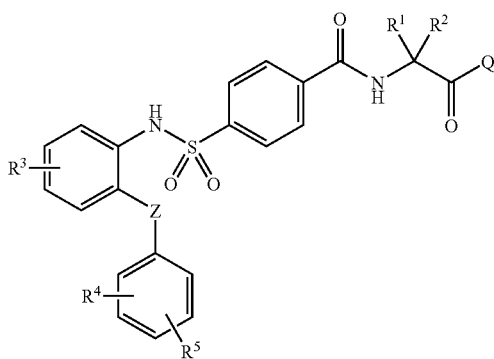
(I)

wherein
$R^1$ is hydrogen atom or $C_1$-$C_4$ alkyl group;
$R^2$ is selected from (1) hydrogen atom; (2) $C_1$-$C_6$ straight or branched alkyl group; (3) —$(CH_2)_n$—$NH_2$; (4) —$(CH_2)_n$—OH; (5) —$(CH_2)_n$—CO—$NH_2$; (6) —$(CH_2)_n$—CO-$OR^c$; (7) benzyl optionally substituted with one or more hydroxy group or halogen atom; or
$R^1$, $R^2$ and the carbon atom to which they are both attached together form a 3-7 membered cycloalkyl ring;
$R^3$, $R^4$ and $R^5$ are independently of each other hydrogen atom; halogen atom; cyano; nitro; amino; or amino substituted with one or more $C_1$-$C_4$ alkyl group; trifluoromethyl; $C_1$-$C_4$ alkyl; $C_1$-$C_4$ alkoxy; trifluoromethoxy; $C_1$-$C_4$ alkoxycarbonyl; —C(=O)—$NH_2$ or hydroxy group;
Z is selected from (1) single bond; (2) oxygen atom; (3) $CH_2$ group; (4) CO group; (5) $NR^c$ group; (6) S atom; (7) $SO_2$ group;
Q is selected from

(1)

optionally substituted with —$(CH_2)_m$—OH group, or —$(CH_2)_n$—X—P group;

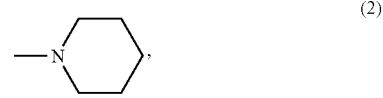
(2)

optionally substituted with one or more $C_1$-$C_4$ alkyl group, one or more halogen atom, —$(CH_2)_m$—OH group, —$(CH_2)_m$—$NH_2$ group, —$(CH_2)_m$—CO—$NH_2$ group, trifluoromethyl group, oxo group, —$(CH_2)_m$—CN group; —NH—CO—($C_1$-$C_4$ alkyl) group, —NH—$SO_2$—($C_1$-$C_4$ alkyl) group, —$(CH_2)_m$—$COOR^e$ group, —CO—$NR^cR^d$ group, —($C_1$-$C_4$ alkoxy) group, —NH—CO—$(CH_2)_m$—$CF_3$ group, —NH—$SO_2$—$CH_2$—$CF_3$ group;

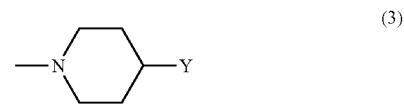
(3)

group;

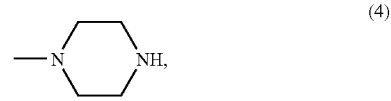
(4)

optionally substituted with oxo group, —$SO_2$—($C_1$-$C_4$ alkyl) group, $C_1$-$C_4$ alkyl group, —CO—($C_1$-$C_4$ alkyl) group, —$(CH_2)_m$—O—$(CH_2)_m$—OH group, —$(CH_2)_m$—OH group, —$SO_2$—$NR^cR^d$ group, —CO—$NR^cR^d$ group;

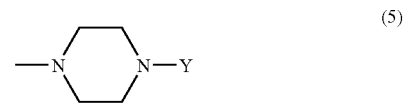
(5)

group;

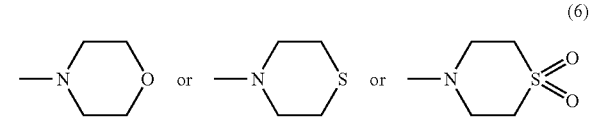
(6)

group;

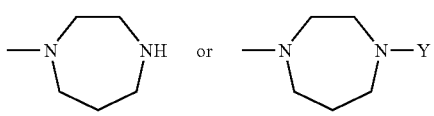

group;

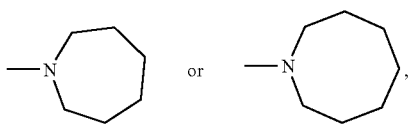

optionally substituted with —(CH$_2$)$_m$—OH group,

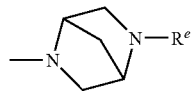

group;

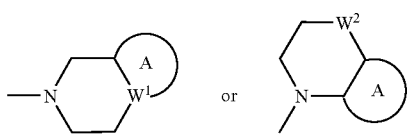

group;

group;
Y is selected from (1) —(CH$_2$)$_n$—NR$^a$R$^b$; (2) —(CH$_2$)$_n$—X—P group;
n is an integer from 0 to 6;
m is an integer from 0 to 3;
X is selected from (1) single bond; (2) oxygen atom; (3) —CO—NR$^c$ group; (4) CO or SO$_2$ group;
P is selected from (1) phenyl group, optionally substituted with one or more halogen atom, hydroxy, cyano, amino or C$_1$-C$_4$ alkyl group; (2) a saturated, partially unsaturated or aromatic 4-7 membered ring containing 1-3 heteroatom selected from O, S, SO$_2$ and N; wherein said ring is optionally substituted with one or more halogen atom, oxo, hydroxy, cyano, amino or C$_1$-C$_4$ alkyl group; (3) C$_5$-C$_8$ cycloalkyl group;
R$^a$ and R$^b$ are (1) hydrogen atom, with the proviso that R$^a$ and R$^b$ can not be simultaneously hydrogen atom; (2) straight or branched C$_1$-C$_6$ alkyl group; (3) R$^a$, R$^b$ and the nitrogen atom to which they are both attached together form a saturated, partially unsaturated or aromatic 4-7 membered ring containing 0-3 heteroatom (in addition to the nitrogen atom to which R$^a$ and R$^b$ attached) selected from O, S, SO$_2$ and N; wherein said ring is optionally substituted with one or more halogen atom, oxo, cyano, hydroxy or C$_1$-C$_4$ alkyl group;
R$^c$ is hydrogen atom or C$_1$-C$_4$ alkyl group;
R$^d$ is hydrogen atom, C$_1$-C$_4$ alkyl group, C$_1$-C$_4$ hydroxyalkyl group, C$_3$-C$_8$ cycloalkyl group;
R$^e$ is hydrogen atom, C$_1$-C$_4$ alkyl group, benzyl group;
A is (1) a C$_4$-C$_7$ cycloalkyl ring; (2) a saturated, partially unsaturated or aromatic 5-7 membered ring containing 0-3 heteroatom selected from O, S, SO$_2$ and N; wherein said ring is optionally substituted with one or more halogen atom, oxo, cyano, hydroxy, amino, phenyl or C$_1$-C$_4$ alkyl group;
B is a saturated, partially unsaturated or aromatic 4-7 membered ring containing 1-3 heteroatom selected from O, S, SO$_2$ and N; wherein said ring is optionally substituted with one or more halogen atom, oxo, cyano, hydroxy, amino, phenyl or C$_1$-C$_4$ alkyl group;
W$^1$ is carbon atom, nitrogen atom, or CH group;
W$^2$ is oxygen atom, sulfur atom, NH, CH$_2$ or SO$_2$ group;
and optical antipodes or racemates and/or salts and/or hydrates and/or solvates thereof.

The invention also relates to the pharmaceutical compositions containing the compounds of formula (I) or optical antipodes or racemates or salts or hydrates or solvates thereof as active ingredient.

Furthermore objects of the present invention are the synthesis of compounds of formula (I), and the chemical and pharmaceutical manufacture of medicaments containing these compounds, as well as the methods of treatment with these compounds, which means administering to a mammal to be treated—including human—effective amount/amounts of compounds of formula (I) of the present invention as such or as medicament.

The term "halogen" substituent denotes fluorine, chlorine, bromine or iodine atoms. The term C$_1$-C$_4$ alkyl group used in the present description denotes methyl, ethyl, normal- and isopropyl and different butyl groups. These C$_1$-C$_4$ alkyl groups can be in the C$_1$-C$_4$ alkoxy groups and C$_1$-C$_4$ hydroxyalkyl groups.

The 4-7 membered heterocyclic ring in the meaning of R$^a$ and R$^b$ can be e.g. piperidine, pyrrolidine, piperazine, homopiperazine, morpholine, thiomorpholine and the like.

The 4-7 membered heterocyclic ring in the meaning of P and B can be e.g. imidazole, triazole, oxazol, thiazole, tetrazole, furan, tetrahydrofuran, pyrimidine, pyridine, piperidine, pyrrolidine, pyrazine, piperazine, homopiperazine, morpholine, thiomorpholine and the like.

The saturated, partially unsaturated or aromatic 5-7 membered ring in the meaning of A can be e.g. imidazole, triazole, oxazol, thiazole, tetrazole, pyrimidine, pyridine, piperidine, pyrrolidine, pyrazine, piperazine, homopiperazine, morpholine, thiomorpholine and the like.

The invention relates also to the salts of compounds of formula (I) formed with acids or bases.

Both organic and inorganic acids can be used for the formation of acid addition salts. Suitable inorganic acids can be e.g. hydrochloric acid, sulfuric acid and phosphoric acid. Representatives of monovalent organic acids can be e.g. formic acid, acetic acid, trifluoroacetic acid, propionic acid, and different butyric acids, valeric acids and capric acids. Representatives of bivalent organic acids can be e.g. oxalic acid, malonic acid, maleic acid, fumaric acid and succinic acid. Other organic acids can also be used, such as hydroxy acids e.g. citric acid, tartaric acid, or aromatic carboxylic acids e.g. benzoic acid or salicylic acid, as well as aliphatic and aromatic sulfonic acids e.g. methanesulfonic acid and p-toluenesulfonic acid. Especially valuable group of the acid addition salts is in which the acid component itself does not have therapeutical effect in the applied dose or it does not have unfavorable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and isolation of the desired compounds.

Among the salts formed with bases especially important are the salts formed with alkali metals, e.g. sodium, potassium, alkaline-earth metals, e.g. calcium and magnesium, as well as with ammonia or organic amines. The latter bases can have further substituents, e.g. hydroxy or amino groups, which can influence e.g. the solubility and the handling of the product. The salts formed with bases are pharmaceutically acceptable base addition salts.

According to the invention the compounds of formula (I) can be synthesized by reacting an amine derivative of formula (II)

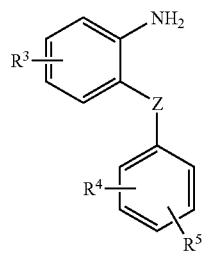
(II)

wherein the meaning of $R^3$, $R^4$ and $R^5$ is as described above for the formula (I)—with sulfonyl chloride of formula (III)

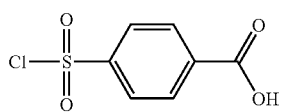
(III)

then the so obtained phenylsulfamoyl benzoic acid derivative of formula (IV)

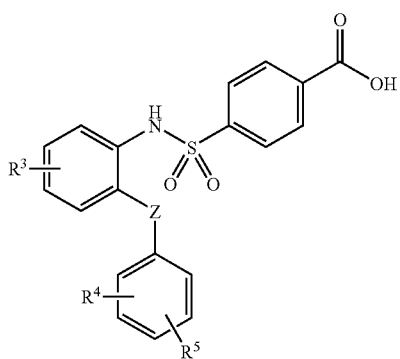
(IV)

wherein the meaning of $R^3$, $R^4$ and $R^5$ is as described above for the formula (I)—is reacted with an amino acid of formula (V)

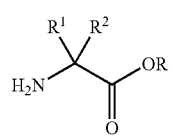
(V)

wherein the meaning of $R^1$ and $R^2$ is as described above for the formula (I) and R is $C_1$-$C_4$ alkyl- and the so obtained compound of formula (VI)

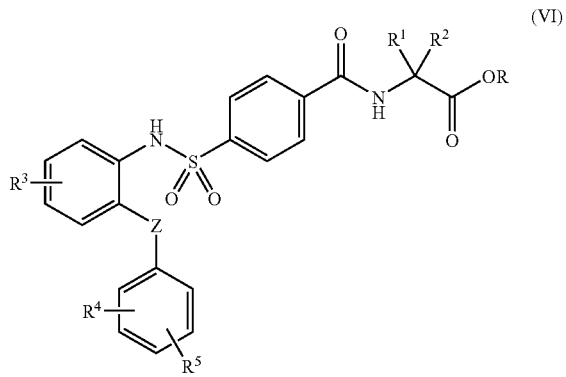
(VI)

wherein the meaning of $R^1$, $R^2$, $R^3$, $R^4$, $R^5$ and R is as defined above—is hydrolyzed to furnish a carboxylic acid derivative of formula (VII)

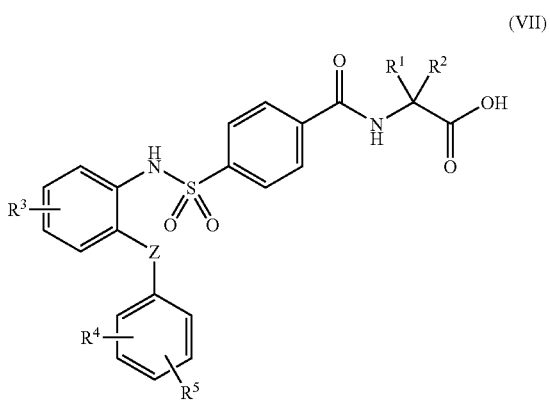
(VII)

wherein the meaning of $R^1$, $R^2$, $R^3$, $R^4$ and $R^5$ is as defined above—finally the latter is reacted with an amine derivative Q and the obtained phenylsulfamoyl benzamide derivative of formula (I) in given case can be transformed into an other compound of formula (I) by introducing new substituents and/or modifying or removing the existing ones, and/or salt formation and/or liberating the compound from salts.

The sulfonylation reaction is preferably carried out in a proper solvent, preferably in the presence of a base. The reactions are followed by thin layer chromatography. The necessary reaction time is 6-20 h. The work-up of the reaction mixture can be carried out by different methods.

a) The reaction mixture is concentrated and the product is isolated by crystallization or extraction. If the crude product is not pure enough, then column chromatography can be used for the purification of it. The column chromatography is carried out either on normal phase using Kieselgel 60 as adsorbent and different solvent systems, e.g. n-hexane/ethyl acetate, chloroform/methanol, dichloromethane/ethyl acetate or chloroform/acetone as eluents, or on reversed phase using YMC-Pack ODS-AQ type packings (produced by YMC) and acetonitrile/water/trifluoroacetic acid or acetonitrile/water/acetic acid as eluent.

b) The reaction mixture is poured into ice-water and the product is isolated by filtration or extraction. The crude product is crystallized or purified by column chromatography as described above. The structures of the products are determined by IR, NMR and mass spectrometry.

Hydrolysis of a compound of formula (VI) can be carried out with a base, e.g. alkali metal hydroxide, preferably sodium or lithium hydroxide, or with an acid, e.g. organic acid, preferably trifluoroacetic acid.

The amide bond formations are preferably carried out by preparing an active derivative from a carboxylic acid of formula (IV) or (VII) which is reacted with an amino acid of formula (V) or an amine Q, respectively, preferably in the presence of a base.

The transformation of a carboxylic acid into an active derivative can be carried out in situ during the amide bond formation in a proper solvent (e.g. to dimethylformamide, acetonitrile, chlorinated hydrocarbons or hydrocarbons or the mixture thereof). The active derivatives can be acid chlorides (e.g. prepared from carboxylic acid with thionyl chloride), mixed anhydrides (e.g. prepared from carboxylic acid with isobutyl chloroformate in the presence of a base, e.g. triethylamine), active esters (e.g. prepared from carboxylic acid with hydroxybenztriazol (HOBt) and dicyclohexyl-carbodiimide (DCC) or O-benzotriazol-1-yl-N,N,N',N'-tetramethyluronium hexafluorophosphate (HBTU) in the presence of a base e.g. triethylamine). The active derivatives can be prepared at a temperature in the range of 0° C. to room temperature. A proper amino acid of formula (V) or an amine Q is added as a base or as a salt formed with inorganic acid to the so obtained solution or suspension in the presence of a base, e.g. triethylamine, needed for the liberation of the amine. The condensation reactions are followed by thin layer chromatography. The necessary reaction time is 6-20 h. The work-up of the reaction mixture can be carried out by different methods.

a) The reaction mixture is concentrated, and the residue is crystallized or extracted with a proper organic solvent and in given case purified by column chromatography. The column chromatography is carried out on normal phase using Kieselgel 60 as adsorbent and different solvent systems, e.g. toluene/methanol, chloroform/methanol or toluene/acetone, as eluents or on reversed phase using YMC-Pack ODS-AQ type packings (produced by YMC) and acetonitrile/water/trifluoroacetic acid or acetonitrile/water/acetic acid as eluent.

b) The reaction mixture is directly purified by column chromatography as described above to yield the pure product.

The structures of the products are determined by IR, NMR and mass spectrometry.

The obtained benzamide derivatives of formula (I)—independently from the method of preparation—in given case can be transformed into another compound of formula (I) by introducing further substituents and/or modifying and/or removing the existing ones, and/or formation of salts with acids and/or liberating the benzamide derivative of formula (I) from the obtained acid addition salts by treatment with a base and/or the free sulfonamide derivative of formula (I) can be transformed into a salt by treatment with a base.

For instance cleaving the benzyl group from N-benzyl group, which stands for $R^e$, can be carried out e.g. with catalytic hydrogenation or with chloroethyl chloroformate in a proper solvent. The compounds of formula (I) containing free hydroxy group can be transformed into acyloxy or sulfoxy derivatives with different acylating or sulfonylating agents. The reactions can be carried out for example in chlorinated hydrocarbons using acid chloride or acid anhydride as acylating agent in the presence of a base (e.g. triethylamine or sodium carbonate). The sulfonamide derivatives of formula (I) containing a nitro group can be transformed into amines by reduction and the amines can be further reacted to give acid amides as described for the acylation of hydroxy groups or carbamate derivatives can be synthesized. Ester groups can be hydrolyzed and the obtained free carboxylic acids can be transformed into amides by reacting with proper amine derivatives. N-(tert-Butoxycarbonyl) group can be cleaved by organic or inorganic acids (e.g. trifluoroacetic acid or hydrogen chloride). Cyano groups can be transformed into amide, N-hydroxy-amidine or different N-containing heterocyclic groups.

Most of the amino acids of formula (V) and amines Q are either commercially available or can be synthesized by different known methods. The syntheses of some new amines Q are described in the Examples. Following these procedures the other amines Q can also be prepared.

The compounds of the present invention as well as their pharmaceutically acceptable salts or hydrates or solvates can be used as such or suitably in the form of pharmaceutical compositions. These compositions (drugs) can be in solid, liquid or semiliquid form and pharmaceutical adjuvant and auxiliary materials can be added, which are commonly used in practice, such as carriers, excipients, diluents, stabilizers, wetting or emulsifying agents, pH- and osmotic pressure-influencing, flavoring or aromatizing, as well as formulation-promoting or formulation-providing additives.

The dosage required to exert the therapeutical effect can vary within wide limits and will be fitted to the individual requirements in each of the particular case, depending on the stage of the disease, the condition and the bodyweight of the patient to be treated, as well as the sensitivity of the patient against the active ingredient, route of administration and number of daily treatments. The actual dose of the active ingredient to be used can safely be determined by the attending physician skilled in the art in the knowledge of the patient to be treated.

The pharmaceutical compositions containing the active ingredient according to the present invention usually contain 0.01 to 100 mg of active ingredient in a single dosage unit. It is, of course possible that the amount of the active ingredient in some compositions exceeds the upper or lower limits defined above.

The solid forms of the pharmaceutical compositions can be e.g. tablets, dragées, capsules, pills or lyophilized powder ampoules useful for the preparation of injections. Liquid compositions are the injectable and infusable compositions, fluid medicines, packing fluids and drops. Semiliquid compositions can be ointments, balsams, creams, shaking mixtures and suppositories.

For the sake of a simple administration it is suitable if the pharmaceutical compositions comprise dosage units containing the amount of the active ingredient to be administered once, or a few multiples or a half, third or fourth part thereof. Such dosage units are e.g. tablets, which can be powdered with grooves promoting the halving or quartering of the tablet in order to exactly administer the required amount of the active ingredient.

Tablets can be coated with an acid-soluble layer in order to assure the release of the active ingredient content after leaving the stomach. Such tablets are enteric-coated. A similar effect can be achieved also by encapsulating the active ingredient.

The pharmaceutical compositions for oral administration can contain e.g. lactose or starch as excipients, sodium carboxymethylcellulose, methylcellulose, polyvinyl pyrrolidine or starch paste as binders or granulating agents. Potato starch or microcrystalline cellulose is added as disintegration agents, but ultraamylopectin or formaldehyde casein can also be used. Talcum, colloidic silicic acid, stearin, calcium or magnesium stearate can be used as antiadhesive and lubricants.

The tablets can be manufactured e.g. by wet granulation, followed by pressing. The mixed active ingredients and excipients, as well as in given case part of the disintegrants are granulated with an aqueous, alcoholic or aqueous alcoholic solution of the binders in an appropriate equipment, then the granulate is dried. The other disintegrants, lubricants and antiadhesive agents are added to the dried granulate, and the mixture is pressed to a tablet. In given case the tablets are made with halving groove to ease the administration.

The tablets can be made directly from the mixture of the active ingredient and the proper auxiliaries by pressing. In given case, the tablets can be coated by using additives commonly used in the pharmaceutical practice, e.g. stabilizers, flavoring, coloring agents, such as sugar, cellulose derivatives (methyl- or ethylcellulose, sodium carboxymethylcellulose, etc), polyvinyl pyrrolidone, calcium phosphate, calcium carbonate, food coloring agents, food laces, aroma agents, iron oxide pigments, etc. In the case of capsules the mixture of the active ingredient and the auxiliaries is filled into capsules.

Liquid oral compositions, e.g. suspensions, syrups, elixirs can be made by using water, glycols, oils, alcohols, coloring and flavoring agents.

For rectal administration the composition is formulated in suppositories or clysters. The suppository can contain beside the active ingredient a carrier, so called adeps pro suppository. Carriers can be vegetable oils, such as hydrogenated vegetable oils, triglycerides of $C_{12}$-$C_{18}$ fatty acids (preferably the carriers under the trade name Witepsol). The active ingredient is homogeneously mixed with the melted adeps pro suppository and the suppositories are moulded.

For parenteral administration the composition is formulated as injection solution. For manufacturing the injection solution the active ingredients are dissolved in distilled water and/or in different organic solvents, such as glycolethers, in given case in the presence of solubilizers, e.g. polioxyethylensorbitane-monolaurate, -monooleate, or monostearate (Tween 20, Tween 60, Tween 80). The injection solution can also contain different auxiliaries, such as conserving agents, e.g. ethylendiamine tetraacetate, as well as pH adjusting agents and buffers and in given case local anaesthetic, e.g. lidocain. The injection solution containing the active ingredient of the invention is filtered before it is filled into ampoules, and it is sterilized after filling.

If the active ingredient is hygroscopic, then it can be stabilized by liophylization.

Utilities

The compounds of the present invention are bradykinin receptor antagonists, in particular selective bradykinin B1 receptor antagonists, consequently are useful in the treatment or prevention of painful and inflammatory processes. The compounds would be effective in the treatment of pain including, e.g., chronic pain, particularly inflammatory pain, hyperalgesia, bone and joint pain (osteoarthritis), repetitive motion pain, myofascial pain (muscular injury, fibromyalgia), visceral pain (ulcerative colitis, pancreatitis, cystitis, uveitis), perioperative pain (general surgery, gynecological), postoperative pain (postsurgical pain syndrome), posttraumatic pain (e.g. sprains or fracture), neuropathic pain (postherpetic neuralgia, nerve injury, phantom limb pain, mononeuropthy, polyneuropathy) dental pain, and cancer pain. Furthermore for the treatment of pain associated with angina, menstruation, diabetic vasculopathy, post capillary resistance or diabetic symptoms associated with insulitis (e.g. hyperglycemia, diuresis, proteinurea and increased nitrite and kallikrein urinary excretion), diabethic hyperalgeisa. Moreover the compounds may be used for the treatment angioedema, atherosclerosis, septic shock e.g. as anti-hypovolemic and/or anti-hypotensive agents, and sepsis. They may be used as smooth muscle relaxants for the treatment of spasm of the gastrointestinal tract or uterus. Further, the compounds of this invention can additionally be used to treat inflammatory skin disorders, such as psoriasis and eczema, and skin injuries including burning and sunburning (UV-erythema and pain). The compounds may be used to treat inflammatory pain of varied origins (e.g. rheumatoid arthritis, rheumatic disease, tenosynovitis, liver disease, irritable bowel syndrome, inflammatory bowel disease, Crohn's disease, nephritis, allergic rhinitis, vasomotor rhinitis, uveitis, gingivitis), allergies. Such compounds may be used therapeutically to treat inflammatory airways disease e.g. chronic obstructive pulmonary disease, adult respiratory distress syndrome, bronchitis, pneumonia, asthma. They may be used to control, restrict or reverse airways hyperreactivity in asthma, to treat intrinsic and extrinsic asthma including allergic asthma (atopic or non-atopic), occupational asthma, viral or bacterial exacerbated asthma, other non-allergic asthmas, "wheezy-infant syndrome", as well as exercise-induced bronchoconstriction. They may be effective against pneumoconiosis, including aluminosis, antracosis, asbestosis, chalicosis, ptilosis, siderosis, silicosis, tabacosis and byssinosis. Additionally, they may be effective in some neurological disorders, e.g. against multiple sclerosis, Alzheimer's disease, epilepsy, cerebral edema, headache including cluster headache, migraine including prophylactic and acute use, as well as closed head trauma.

Biological Evaluation

Functional Assay:

Assessment of Antagonist Potency at B1 and B2 Receptors In Vitro by Measurement of Cytosolic Calcium Ion Concentration with a Plate Reader Fluorimeter in Cells Expressing Recombinant Human B1 or B2 Receptors Cell Culture Chinese hamster ovary (CHO) cells stably expressing recombinant human B1 (CHO-B1, Euroscreen) or B2 (CHO-B2, Perkin-Elmer) receptors were cultured in Dulbecco's Modified Eagle's Medium (DMEM) containing 10% Fetal Calf Serum (FCS), 100 U/ml penicillin, 0.1 mg/ml streptomycin, 0.25 µg/ml amphotericin B, 1% Minimum Essential Medium Eagle (MEM), non essential amino acid solution, 600 µg/ml G418, 1% pyruvate (for the B2 cell line). Cells were kept at 37° C. in a humidified incubator in an atmosphere of 5% $CO_2$/95% air and were passaged 1:4 three times a week. Cells were plated at 1.5-2.5×$10^4$ cell/well on standard 96-well microplates, measurements of cytosolic calcium ion concentration ($[Ca^{2+}]_i$) were carried out 1-2 days after cell plating.

Fluorimetric Measurement of Cytosolic Calcium Concentration

Measurements of $[Ca^{2+}]_i$ were carried out on CHO-B1 and CHO-B2 cells stably expressing human B1 and B2 receptors, respectively. Cells were grown in standard 96-well microplates and before the measurement were loaded with a fluorescent $Ca^{2+}$-sensitive dye, fluo-4/AM (2 µM): after removing the culture medium the dye was added to the cells (dissolved in assay buffer: 145 mM NaCl, 5 mM KCl, 2 mM $MgCl_2$, 2 mM $CaCl_2$, 10 mM HEPES, 20 mM D-glucose, 2 mM probenecid, 100 µl/well) and cells were incubated at 37° C. in a humidified incubator in an atmosphere of 5% $CO_2$/95% air for 40-120 min. To stop dye loading cells were washed twice with assay buffer. After washing, various concentrations of the test compounds (diluted in extracellular medium from a DMSO stock solution, final DMSO concentration was <0.1%) or buffer were added to each well depending on the experimental setup. After incubation at 37° C. for 20-25 min. baseline and agonist-evoked changes of $[Ca^{2+}]_i$ were measured column by column with a plate reader fluorimeter (Fluoroskan Ascent, Labsystems). Excitation and detection of emission was carried out from the bottom of the plate. Filters used for Fluo-4: excitation filter—485 nm, emission filter—538 nm. The whole measurement process was performed at 37° C. and was controlled by custom software. Inhibitory potency of the test compounds was assessed by measuring the reduction in the agonist-evoked $[Ca^{2+}]_i$-elevation in the presence of different concentrations of the compounds. The agonists were LysDABK for CHO-B1, and bradykinin for CHO-B2 cells. Agonists were applied at an $EC_{80}$ concentration, the $EC_{80}$-values were derived from daily determined dose-response curves. Fluorescence data were expressed as ΔF/F (fluorescence change normalized to baseline). All treatments on a single plate were measured in multiple wells. Data from all wells with the same treatment were averaged and the average values were used for analysis. Inhibitory potency of a compound at a single concentration point was expressed as percent inhibition of the control agonist response. Sigmoidal concentration-inhibition curves were fitted to the data (derived from at least three independent experiments) and $IC_{50}$-values were determined as the concentration that produces half of the maximal inhibition caused by the compound.

The examined reference compounds measured in functional and binding tests are the following:
1) 4-{2-[(2,2-diphenyl-ethyl)-amino]-5-{-4-[4-[(4-methyl-1-piperazinyl)-carbonyl]-1-piperidinyl]-sulfonyl}-benzoyl}-morfoline (NVP-SAA164, Br. J. Pharmacol. 144 (2005) 889-899); $K_i$ 8 nM; $IC_{50}$: 33 nM;
2) (R)—N-[2,3-dihydro-2-oxo-5-(2-phenyl-ethyl)-1-propyl-1H-1,4-benzodiazepin-3-yl]-N'-{4-[4-(4-pyridinyl)-1-piperazinyl]-phenyl}-urea (J. Med. Chem. 46 (2003) 1803-1806); $K_i$ 0.59 nM; $IC_{50}$ 1.9 nM;
3) N-[4-(,4'-bipiperidin)-1'-ylphenyl]-N'-[(3R)-2,3-dihydro-5-(4-methyl-phenyl)-2-oxo-1-propyl-1H-1,4-benzodiazepin-3-yl]-urea (J. Med. Chem. 46 (2003) 1803-1806); $K_i$ 13.4 nM; $IC_{50}$ 64.5 nM The $K_i$ and $IC_{50}$ data measured by us for the reference compounds are in good agreement with the data given in the literature.

In Table I the most effective compounds of this invention measured in functional assay are listed.

TABLE I

| Number of example | B1 func. |
|---|---|
| 1.1 | ++++ |
| 1.2 | ++++ |
| 1.3 | ++++ |
| 1.4 | ++++ |
| 1.5 | ++++ |
| 1.6 | ++++ |
| 1.7 | ++++ |
| 1.8 | ++++ |
| 1.9 | ++++ |
| 1.10 | ++++ |
| 1.11 | ++++ |
| 1.12 | ++++ |
| 1.13 | ++++ |
| 1.21 | ++++ |
| 1.22 | ++++ |
| 2.2 | ++++ |
| 2.3 | ++++ |
| 2.4 | ++++ |
| 2.5 | ++++ |
| 2.6 | ++++ |
| 2.7 | ++++ |
| 2.10 | +++ |
| 2.15 | +++ |
| 2.22 | ++++ |
| 2.34 | ++++ |
| 3.1 | ++++ |
| 3.2 | ++++ |
| 3.3 | ++++ |
| 3.4 | ++++ |
| 3.5 | ++++ |
| 3.6 | ++++ |
| 3.7 | ++++ |
| 3.8 | ++++ |
| 3.9 | ++++ |
| 3.10 | ++++ |
| 3.13 | ++++ |
| 3.14 | ++++ |
| 3.15 | ++++ |
| 3.16 | ++++ |
| 3.17 | ++++ |
| 11.1 | ++++ |
| 11.2 | ++++ |
| 11.3 | ++++ |
| 11.4 | ++++ |
| 11.5 | ++++ |
| 11.6 | ++++ |
| 11.7 | ++++ |

+ $IC_{50}$ > 0.5 μM
++ $IC_{50}$ is between 0.1 and 0.5 μM
+++ $IC_{50}$ is between 20 and 100 nM
++++ $IC_{50}$ < 20 nM Receptor Binding Assays 1. Human Recombinant Bradykinin B1 Receptor Binding Binding assays were carried out on human recombinant bradykinin) receptors (expressed in CHO cells) according to the Euroscreen Technical Data Sheet (Cat.No.:ES-091). 20 μg protein/tube was incubated with [3,4-prolyl-3,4-$^3$H(N)]-[Des-Arg$^{10}$] Kallidin as radioligand. Non specific binding was determined in the presence of 10 μM Lys-des-Arg$^9$-Bradykinin. The final incubation volume was 250 μl. Samples were incubated for 15 min. at 25° C. then were rapidly vacuum filtered through GF/B filters presoaked for at least 1 h in 0.5% PEI. Radioactivity was determined by liquid scintillation spectroscopy.

In Table II the most effective compounds of this invention measured in binding assay are listed.

TABLE II

| Number of example | B1 binding |
|---|---|
| 1.1 | ++++ |
| 1.2 | ++++ |
| 1.3 | ++++ |
| 1.4 | ++++ |
| 1.5 | ++++ |
| 1.6 | ++++ |
| 1.7 | ++++ |
| 1.8 | ++++ |
| 1.9 | ++++ |
| 1.10 | ++++ |
| 1.11 | ++++ |
| 1.12 | ++++ |
| 1.13 | ++++ |
| 1.21 | ++++ |
| 1.22 | ++++ |
| 2.2 | ++++ |
| 2.3 | ++++ |
| 2.4 | ++++ |
| 2.5 | ++++ |
| 2.6 | ++++ |
| 2.7 | ++++ |
| 2.10 | +++ |
| 2.15 | +++ |

TABLE II-continued

| Number of example | B1 binding |
|---|---|
| 2.22 | ++++ |
| 2.34 | ++++ |
| 3.1 | ++++ |
| 3.2 | ++++ |
| 3.3 | ++++ |
| 3.4 | ++++ |
| 3.5 | ++++ |
| 3.6 | ++++ |
| 3.7 | ++++ |
| 3.8 | ++++ |
| 3.9 | ++++ |
| 3.10 | ++++ |
| 3.13 | ++++ |
| 3.14 | ++++ |
| 3.15 | ++++ |
| 3.16 | ++++ |
| 3.17 | ++++ |
| 11.1 | +++ |
| 11.2 | +++ |
| 11.3 | ++++ |
| 11.4 | ++++ |
| 11.5 | ++++ |
| 11.6 | ++++ |
| 11.7 | ++++ |

+ $K_i > 0.5$ μM
++ $K_i$ is between 0.1 and 0.5 μM
+++ $K_i$ is between 20 and 100 nM
++++ $K_i < 20$ nM 2. Human Recombinant Bradykinin B2 Receptor Binding Binding assays were carried out on human recombinant bradykinin2 receptors (expressed in CHO cells) according to the Receptor Biology Technical Data Sheet (Cat.No.: RBHB2M) with minor modifications. 8.4 μg protein/tube was incubated with [2,3,-prolyl-3,4-$^3$H(N)]-Bradykinin as radioligand. Non specific binding was determined in the presence of 5 μM bradykinin. The final incubation volume was 200 μl. Samples were incubated for 90 min. at +4° C. then were rapidly vacuum filtered through GF/B filters presoaked for at least 1 h in 0.5% PEI. Radioactivity was determined by liquid scintillation spectroscopy.

The compounds exhibited high affinity and selectivity (>50 fold) for the human B1 receptor over the human B2 receptor according to both functional and binding assays.

The synthesis of compounds and pharmaceutical compositions according to the invention is illustrated by the following not limiting Examples.

Reference Example 1

(4-Methyl-piperazin-1-yl)-piperidin-4-yl-methanone hydrochloride a) 4-(4-Methyl-piperazine-1-carbonyl)-piperidine-1-carboxylic acid tert-butyl ester The solution of 1-(tert-butoxycarbonyl)-4-piperidinecarboxylic acid (Aldrich) (21.88 g, 95.4 mmol), triethylamine (13.3 mL, 95.4 mmol) and HBTU [O-benzotriazol-1-yl-N,N,N',N'-tetramethyluronium hexafluorophosphate (Advanced Chem. Tech.)] (38.36 g, 101.0 mmol) in dry dimethylformamide (100 mL) was stirred at room temperature for five minutes before N-methyl-piperazine (10.6 mL, 95.5 mmol) was added. The pH of the reaction mixture was adjusted to 8 by the addition of triethylamine, the so obtained mixture was stirred at room temperature overnight, then concentrated in vacuo. The residue was treated with saturated sodium hydrogencarbonate solution (350 mL), extracted with ethyl acetate (3×250 mL), the combined organic layers were washed with saturated sodium hydrogencarbonate solution, water and brine, dried over sodium sulfate, filtered and concentrated. The residue was submitted to column chromatography using Kieselgel 60 (0.040-0.063 mm) (Merck) as adsorbent, and chloroform:methanol=9:1 as eluent to yield 25.8 g (87%) of the title compound as an oil.

b) (4-Methyl-piperazin-1-yl)-piperidin-4-yl-methanone hydrochloride

A mixture of 4-(4-methyl-piperazine-1-carbonyl)-piperidine-1-carboxylic acid tert-butyl ester (25.8 g, 82.8 mmol), dry dioxane (500 mL) and 6.5 N hydrogen chloride in dioxane (275 mL) was stirred at room temperature overnight, then diluted with diethyl ether and stirred at 0° C. for 1 h. The precipitated crystals were filtered off, washed with diethyl ether and dried to yield 12.44 g (54%) of the title compound. Mp: 305-307° C. (decomposition).

Example 1.1

4-[2-(2,4-Dichloro-phenoxy)-phenylsulfamoyl]-N-{2-oxo-2-[4-(2-pyrrolidin-1-yl-ethyl)-piperazin-1-yl]-ethyl}-benzamide a) 2,4-Dichloro-1-(2-nitro-phenoxy)-benzene A mixture of 1-fluoro-2-nitrobenzene (4.8 mL, 45.42 mmol), potassium carbonate (13.8 g, 0.1 mol) and 2,4-dichloro-phenol (8.16 g, 50.06 mmol) in dry dimethylformamide (70 mL) was stirred at 100° C. for 2 h. Solids were filtered off, and the filtrate was concentrated in vacuo. The residue was partitioned between diethyl ether and 1N sodium hydroxide, the organic layer was washed with 1N sodium hydroxide, water and brine, dried over sodium sulfate, filtered and concentrated in vacuo to yield 11.69 g (91%) of the title compound as a yellowish oil, which solidifies on standing. Mp: 58-59° C. MS (EI) 285.2 (MH$^+$). Lit. [*Chem. Heterocycl. Compd.* (*Engl. Transl.*) 11 (1975) 1356-1358] Mp: 57-58° C.

b) 2-(2,4-Dichloro-phenoxy)-phenylamine [*Chem. Abstr.* 84 (1976) 164313q]

To a stirred solution of 2,4-dichloro-1-(2-nitro-phenoxy)-benzene (3.5 g, 12.32 mmol) in ethyl acetate (60 mL) stannous chloride dihydrate (13.89 g, 61.6 mmol) was added and the mixture was refluxed for 2 h before it was quenched with saturated sodium hydrogencarbonate solution (192 mL). The organic phase was separated and the aqueous phase was washed several times with ethyl acetate. The combined extracts were dried over sodium sulfate, filtered and concentrated in vacuo to yield 3.1 g (99%) of the title compound as a yellowish oil: MS (EI) 255.2 (MH$^+$).

c) 4-[2-(2,4-Dichloro-phenoxy)-phenylsulfamoyl]-benzoic acid

Under an atmosphere of argon to an ice cooled solution of 2-(2,4-dichloro-phenoxy)-phenylamine (0.5 g, 1.97 mmol) in dry pyridine (5 mL) 4-chlorosulfonyl benzoic acid (0.45 g, 1.97 mmol) was added portion-wise. The reaction mixture was stirred at room temperature overnight. The mixture was evaporated in vacuo, the residue was treated with 1N hydrochloric acid (20 mL), and extracted with ethyl acetate (3×50 mL). The combined organic layers were washed with 1N hydrochloric acid, water and brine, dried over sodium sulfate, filtered and concentrated in vacuo. The residue was submitted to flash column chromatography using Kieselgel 60 (0.015-0.040 mm) as adsorbent (Merck) and chloroform:methanol: acetic acid=294:6:1 as eluent to yield 0.6 g (70%) of the title compound as a light pink solid, which was crystallized from diethyl ether-petroleum ether. MS (EI) 439.3 (MH$^+$).

d) {4-[2-(2,4-Dichloro-phenoxy)-phenylsulfamoyl]-benzoylamino}-acetic acid ethyl ester The solution of 4-[2-(2,4-dichloro-phenoxy)-phenylsulfamoyl]-benzoic acid (8.207 g, 18.7 mmol), triethylamine (5.2 mL, 37.4 mmol) and HBTU (8.24 g, 21.7 mmol) in dry dimethyl formamide (150 mL) was stirred at room temperature for five minutes before glycine ethyl ester hydrochloride (Aldrich) (2.614 g, 18.7 mmol) was added. The pH of the reaction mixture was adjusted to 8 by the addition of triethylamine, the so obtained mixture was stirred at room temperature overnight, then concentrated in vacuo. The residue was treated with saturated sodium hydrogencarbonate solution (300 mL), the precipitated crystals were filtered off, washed with water and dried. The crude product was purified by column chromatography using Kieselgel 60 (0.040-0.063 mm) (Merck) as adsorbent, and n-hexane:ethyl acetate=2:1 as eluent to yield 7.68 g (78%) of the title compound. MS (EI) 524 (MH$^+$).

e) {4-[2-(2,4-Dichloro-phenoxy)-phenylsulfamoyl]-benzoylamino}-acetic acid

To a stirred solution of {4-[2-(2,4-dichloro-phenoxy)-phenylsulfamoyl]-benzoylamino}-acetic acid ethyl ester (7.68 g, 14.67 mmol) in a mixture of tetrahydrofuran (36 mL), water (18 mL) and methanol (18 mL) lithium hydroxide monohydrate (3.09 g, 73.64 mmol) was added and the reaction mixture was stirred at room temperature for 2 h. The mixture was concentrated, the residue was dissolved in water, acidified with 1M hydrochloric acid, the precipitated solid was filtered off, washed with water and dried to yield 6.76 g (93%) of the title compound as a yellowish solid. MS (EI) 496.2 (MH$^+$).

f) 4-[2-(2,4-Dichloro-phenoxy)-phenylsulfamoyl]-N-{2-oxo-2-[4-(2-pyrrolidin-1-yl-ethyl)-piperazin-1-yl]-ethyl}-benzamide To a stirred solution of {4-[2-(2,4-dichloro-phenoxy)-phenylsulfamoyl]-benzoylamino}-acetic acid (42 mg, 0.085 mmol) in a mixture of dichloromethane (2 mL) and dimethylformamide (0.2 mL) 1-(2-pyrrolidin-1-yl-ethyl)-piperazine (EMKA-Chemie) (18 mg, 0.1 mmol), HBTU (46 mg, 0.12 mmol) and triethylamine (60 µL, 0.4 mmol) were added. The mixture was stirred at room temperature for 24 h, then purified by column chromatography using Kieselgel 60 (0.015-0.040 mm) as adsorbent (Merck) and gradient elution starting with 100% A eluent and processing to a mixture of 70% A and 30% B eluent over a period of 15 minutes (eluent A: chloroform; eluent B: methanol containing 5% of ammonium hydroxide) to yield 45.8 mg (82%) of the title compound. MS (EI) 661.2 (MH$^+$).

Compounds of Table 1 were prepared from {4-[2-(2,4-dichloro-phenoxy)-phenylsulfamoyl]-benzoylamino}-acetic acid (Example 1.1/e) according to the method described in Example 1.1/f.

TABLE 1

| Example | Name | MS (EI) (MH$^+$) |
|---|---|---|
| 1.2 | 4-[2-(2,4-Dichloro-phenoxy)-phenylsulfamoyl]-N-{2-[4-(2-dimethylamino-ethyl)-piperazin-1-yl]-2-oxo-ethyl}-benzamide | 635.2 |
| 1.3 | 4-[2-(2,4-Dichloro-phenoxy)-phenylsulfamoyl]-N-{2-[4-(2-diethylamino-ethyl)-piperazin-1-yl]-2-oxo-ethyl}-benzamide | 663.2 |
| 1.4 | 4-[2-(2,4-Dichloro-phenoxy)-phenylsulfamoyl]-N-{2-oxo-2-[4-(3-pyrrolidin-1-yl-propyl)-piperazin-1-yl]-ethyl}-benzamide | 675.2 |
| 1.5 | 4-[2-(2,4-Dichloro-phenoxy)-phenylsulfamoyl]-N-{2-[4-(1-methyl-piperidin-3-ylmethyl)-piperazin-1-yl]-2-oxo-ethyl}-benzamide | 675.2 |
| 1.6 | 4-[2-(2,4-Dichloro-phenoxy)-phenylsulfamoyl]-N-{2-oxo-2-[4-(2-pyrrolidin-1-yl-ethyl)-piperidin-1-yl]-ethyl}-benzamide | 660.2 |
| 1.7 | 4-[2-(2,4-Dichloro-phenoxy)-phenylsulfamoyl]-N-[2-oxo-2-(4-pyrimidin-2-yl-piperazin-1-yl)-ethyl]-benzamide | 642.1 |
| 1.8 | 4-[2-(2,4-Dichloro-phenoxy)-phenylsulfamoyl]-N-{2-[4-(3-morpholin-4-yl-propyl)-[1,4]diazepan-1-yl]-2-oxo-ethyl}-benzamide | 705.2 |
| 1.9 | 4-[2-(2,4-Dichloro-phenoxy)-phenylsulfamoyl]-N-{2-oxo-2-[4-(3-piperidin-1-yl-propyl)-piperazin-1-yl]-ethyl}-benzamide | 689.2 |
| 1.10 | 4-[2-(2,4-Dichloro-phenoxy)-phenylsulfamoyl]-N-{2-[4-(3-dimethylamino-propyl)-piperazin-1-yl]-2-oxo-ethyl}-benzamide | 649.2 |
| 1.11 | 4-[2-(2,4-Dichloro-phenoxy)-phenylsulfamoyl]-N-{2-oxo-2-[4-(3-pyrrolidin-1-yl-propyl)-[1,4]diazepan-1-yl]-ethyl}-benzamide | 689.2 |
| 1.12 | 4-[2-(2,4-Dichloro-phenoxy)-phenylsulfamoyl]-N-{2-[4-(3-morpholin-4-yl-propyl)-piperazin-1-yl]-2-oxo-ethyl}-benzamide | 691.2 |
| 1.13 | 4-[2-(2,4-Dichloro-phenoxy)-phenylsulfamoyl]-N-{2-oxo-2-[4-(2-piperidin-1-yl-ethyl)-piperazin-1-yl]-ethyl}-benzamide | 675.2 |
| 1.14 | 4-[2-(2,4-Dichloro-phenoxy)-phenylsulfamoyl]-N-{2-oxo-2-[4-(2-oxo-2-pyrrolidin-1-yl-ethyl)-piperazin-1-yl]-ethyl}-benzamide | 675.2 |
| 1.15 | 4-[2-(2,4-Dichloro-phenoxy)-phenylsulfamoyl]-N-{2-[4-(2-morpholin-4-yl-ethyl)-piperazin-1-yl]-2-oxo-ethyl}-benzamide | 677.2 |
| 1.16 | 4-[2-(2,4-Dichloro-phenoxy)-phenylsulfamoyl]-N-{2-oxo-2-[4-(2-oxo-2-piperidin-1-yl-ethyl)-piperazin-1-yl]-ethyl}-benzamide | 689.2 |

TABLE 1-continued

| Example | Name | MS (EI) (MH+) |
|---|---|---|
| 1.17 | 4-[2-(2,4-Dichloro-phenoxy)-phenylsulfamoyl]-N-(2-{4-[(methyl-phenyl-carbamoyl)-methyl]-piperazin-1-yl}-2-oxo-ethyl)-benzamide | 711.2 |
| 1.18 | 4-[2-(2,4-Dichloro-phenoxy)-phenylsulfamoyl]-N-{2-[4-(2-morpholin-4-yl-2-oxo-ethyl)-piperazin-1-yl]-2-oxo-ethyl}-benzamide | 691.2 |
| 1.19 | 4-[2-(2,4-Dichloro-phenoxy)-phenylsulfamoyl]-N-[2-oxo-2-(2,3,5,6-tetrahydro-[1,2']bipyrazinyl-4-yl)-ethyl]-benzamide | 642.2 |
| 1.20 | 4-[2-(2,4-Dichloro-phenoxy)-phenylsulfamoyl]-N-{2-[4-(4-methyl-piperazine-1-carbonyl)-piperidin-1-yl]-2-oxo-ethyl}-benzamide | 689.2 |
| 1.21 | 4-[2-(2,4-Dichloro-phenoxy)-phenylsulfamoyl]-N-[2-oxo-2-(4-pyrrolidin-1-yl-piperidin-1-yl)-ethyl]-benzamide | 632.2 |
| 1.22 | 4-[2-(2,4-Dichloro-phenoxy)-phenylsulfamoyl]-N-[2-(4-hydroxy-piperidin-1-yl)-2-oxo-ethyl]-benzamide | 579.2 |
| 1.23 | 4-[2-(2,4-Dichloro-phenoxy)-phenylsulfamoyl]-N-(2-{4-[2-(2-hydroxy-ethoxy)-ethyl]-piperazin-1-yl}-2-oxo-ethyl)-benzamide | 652.2 |
| 1.24 | 4-[2-(2,4-Dichloro-phenoxy)-phenylsulfamoyl]-N-[2-oxo-2-(4-phenyl-piperazin-1-yl)-ethyl]-benzamide | 640.2 |
| 1.25 | N-(2-[1,4']Bipiperidinyl-1'-yl-2-oxo-ethyl)-4-[2-(2,4-dichloro-phenoxy)-phenylsulfamoyl]-benzamide | 646.2 |
| 1.26 | 4-[2-(2,4-Dichloro-phenoxy)-phenylsulfamoyl]-N-(2-oxo-2-piperidin-1-yl-ethyl)-benzamide | 563.2 |
| 1.27 | 4-[2-(2,4-Dichloro-phenoxy)-phenylsulfamoyl]-N-[2-oxo-2-(4-oxo-piperidin-1-yl)-ethyl]-benzamide | 577.1 |
| 1.28 | N-(2-Azepan-1-yl-2-oxo-ethyl)-4-[2-(2,4-dichloro-phenoxy)-phenylsulfamoyl]-benzamide | 577.1 |
| 1.29 | 4-[2-(2,4-Dichloro-phenoxy)-phenylsulfamoyl]-N-(2-oxo-2-pyrrolidin-1-yl-ethyl)-benzamide | 549.1 |
| 1.30 | 4-[2-(2,4-Dichloro-phenoxy)-phenylsulfamoyl]-N-(2-morpholin-4-yl-2-oxo-ethyl)-benzamide | 565.1 |
| 1.31 | N-[2-(4-Cyano-piperidin-1-yl)-2-oxo-ethyl]-4-[2-(2,4-dichloro-phenoxy)-phenylsulfamoyl]-benzamide | 588.1 |
| 1.32 | 4-[2-(2,4-Dichloro-phenoxy)-phenylsulfamoyl]-N-[2-oxo-2-(4-trifluoromethyl-piperidin-1-yl)-ethyl]-benzamide | 631.1 |
| 1.33 | 4-[2-(2,4-Dichloro-phenoxy)-phenylsulfamoyl]-N-(2-oxo-2-thiomorpholin-4-yl-ethyl)-benzamide | 581.1 |
| 1.34 | 4-[2-(2,4-Dichloro-phenoxy)-phenylsulfamoyl]-N-[2-(4-methyl-piperidin-1-yl)-2-oxo-ethyl]-benzamide | 577.1 |
| 1.35 | N-[2-(4-Benzoyl-piperazin-1-yl)-2-oxo-ethyl]-4-[2-(2,4-dichloro-phenoxy)-phenylsulfamoyl]-benzamide | 668.1 |
| 1.36 | 4-[2-(2,4-Dichloro-phenoxy)-phenylsulfamoyl]-N-{2-[4-(furan-2-carbonyl)-piperazin-1-yl]-2-oxo-ethyl}-benzamide | 658.1 |
| 1.37 | 4-[2-(2,4-Dichloro-phenoxy)-phenylsulfamoyl]-N-[2-(4-ethanesulfonyl-piperazin-1-yl)-2-oxo-ethyl]-benzamide | 656.1 |
| 1.38 | 1-(2-{4-[2-(2,4-Dichloro-phenoxy)-phenylsulfamoyl]-benzoylamino}-acetyl)-piperidine-4-carboxylic acid amide | 606.1 |
| 1.39 | 4-[2-(2,4-Dichloro-phenoxy)-phenylsulfamoyl]-N-[2-(3-hydroxymethyl-piperidin-1-yl)-2-oxo-ethyl]-benzamide | 593.2 |
| 1.40 | 4-[2-(2,4-Dichloro-phenoxy)-phenylsulfamoyl]-N-[2-oxo-2-(3-oxo-piperazin-1-yl)-ethyl]-benzamide | 578.1 |
| 1.41 | 4-[2-(2,4-Dichloro-phenoxy)-phenylsulfamoyl]-N-[2-(4-hydroxymethyl-piperidin-1-yl)-2-oxo-ethyl]-benzamide | 593.1 |
| 1.42 | 4-[2-(2,4-Dichloro-phenoxy)-phenylsulfamoyl]-N-{2-[4-(2-hydroxy-ethyl)-piperidin-1-yl]-2-oxo-ethyl}-benzamide | 607.1 |
| 1.43 | 4-[2-(2,4-Dichloro-phenoxy)-phenylsulfamoyl]-N-[2-(3-hydroxy-pyrrolidin-1-yl)-2-oxo-ethyl]-benzamide | 565.1 |
| 1.44 | N-[2-(4-Acetyl-piperazin-1-yl)-2-oxo-ethyl]-4-[2-(2,4-dichloro-phenoxy)-phenylsulfamoyl]-benzamide | 606.1 |
| 1.45 | 4-[2-(2,4-Dichloro-phenoxy)-phenylsulfamoyl]-N-{2-oxo-2-[4-(tetrahydro-furan-2-carbonyl)-piperazin-1-yl]-ethyl}-benzamide | 662.1 |
| 1.46 | 4-[2-(2,4-Dichloro-phenoxy)-phenylsulfamoyl]-N-{2-[4-(3-hydroxy-phenyl)-piperazin-1-yl]-2-oxo-ethyl}-benzamide | 656.1 |
| 1.47 | 4-[2-(2,4-Dichloro-phenoxy)-phenylsulfamoyl]-N-[2-(1,1-dioxo-1$\lambda^6$-thiomorpholin-4-yl)-2-oxo-ethyl]-benzamide | 613 |
| 1.48 | N-[2-(4-Cyclopropylmethyl-piperazin-1-yl)-2-oxo-ethyl]-4-[2-(2,4-dichloro-phenoxy)-phenylsulfamoyl]-benzamide | 618.2 |
| 1.49 | 4-[2-(2,4-Dichloro-phenoxy)-phenylsulfamoyl]-N-[2-(4-ethyl-piperazin-1-yl)-2-oxo-ethyl]-benzamide | 592.1 |

Example 2.1

N-{2-Oxo-2-[(S)-2-(piperazine-1-carbonyl)-pyrrolidin-1-yl]-ethyl}-4-(2-phenoxy-phenylsulfamoyl)-benzamide hydrochloride a) 4-(2-Phenoxy-phenylsulfamoyl)-benzoic acid

The title compound was prepared from 2-phenoxy-phenylamine (Aldrich) according to the method described in Example 1.1/c. MS (EI) 370.2 (MH$^+$).

b) [4-(2-Phenoxy-phenylsulfamoyl)-benzoylamino]-acetic acid ethyl ester

The title compound was prepared from 4-(2-phenoxy-phenylsulfamoyl)-benzoic acid and glycine ethyl ester hydrochloride (Aldrich) according to the method described in Example 1.1/d. MS (EI) 455.2 (MH$^+$).

c) [4-(2-Phenoxy-phenylsulfamoyl)-benzoylamino]-acetic acid

The title compound was prepared from [4-(2-phenoxy-phenylsulfamoyl)-benzoylamino]-acetic acid ethyl ester according to the method described in Example 1.1/e. MS (EI) 427.2 (MH$^+$).

d) (S)-1-{2-[4-(2-Phenoxy-phenylsulfamoyl)-benzoylamino]-acetyl}-pyrrolidine-2-carboxylic acid benzyl ester The title compound was prepared from [4-(2-phenoxy-phenylsulfamoyl)-benzoylamino]-acetic acid and L-proline benzyl ester hydrochloride according to the method described in Example 1.1/d. MS (EI) 614.3 (MH$^+$).

e) (S)-1-{2-[4-(2-Phenoxy-phenylsulfamoyl)-benzoylamino]-acetyl}-pyrrolidine-2-carboxylic acid The title compound was prepared from (S)-1-{2-[4-(2-phenoxy-phenylsulfamoyl)-benzoylamino]-acetyl}-pyrrolidine-2-carboxylic acid benzyl ester according to the method described in Example 1.1/e. MS (EI) 524.2 (MH$^+$).

f) 4-((S)-1-{2-[4-(2-Phenoxy-phenylsulfamoyl)-benzoylamino]-acetyl}-pyrrolidine-2-carbonyl)-piperazine-1-carboxylic acid tert-butyl ester The title compound was prepared from (S)-1-{2-[4-(2-phenoxy-phenylsulfamoyl)-benzoylamino]-acetyl}-pyrrolidine-2-carboxylic acid and piperazine-1-carboxylic acid tert-butyl ester according to the method described in Example 1.1/d. MS (EI) 714.3 (M+Na$^+$).

g) N-{2-Oxo-2-[(S)-2-(piperazine-1-carbonyl)-pyrrolidin-1-yl]-ethyl}-4-(2-phenoxy-phenylsulfamoyl)-benzamide hydrochloride To a stirred solution of 4-((S)-1-{2-[4-(2-phenoxy-phenylsulfamoyl)-benzoylamino]-acetyl}-pyrrolidine-2-carbonyl)-piperazine-1-carboxylic acid tert-butyl ester (0.115 g, 0.166 mmol) in dichloromethane (2 mL) 9 M hydrogen chloride in ethanol (0.2 mL) was added. The reaction mixture was stirred at room temperature for 2 h, then diethyl ether (20 mL) was added, the precipitated crystals were filtered, washed with diethyl ether and dried to yield 0.089 g (89%) of the title compound. MS (EI) 592.2 (MH$^+$).

Compounds of Table 2 were prepared from [4-(2-phenoxy-phenylsulfamoyl)-benzoylamino]-acetic acid (Example 2.1/c) according to the method described in Example 1.1/f.

TABLE 2

| Example | Name | MS (EI) (MH$^+$) |
|---|---|---|
| 2.2 | N-{2-Oxo-2-[4-(2-pyrrolidin-1-yl-ethyl)-piperazin-1-yl]-ethyl}-4-(2-phenoxy-phenylsulfamoyl)-benzamide | 592.2 |
| 2.3 | N-{2-[4-(2-Dimethylamino-ethyl)-piperazin-1-yl]-2-oxo-ethyl}-4-(2-phenoxy-phenylsulfamoyl)-benzamide | 566.2 |
| 2.4 | N-{2-[4-(2-Diethylamino-ethyl)-piperazin-1-yl]-2-oxo-ethyl}-4-(2-phenoxy-phenylsulfamoyl)-benzamide | 594.2 |
| 2.5 | N-{2-Oxo-2-[4-(3-pyrrolidin-1-yl-propyl)-piperazin-1-yl]-ethyl}-4-(2-phenoxy-phenylsulfamoyl)-benzamide | 606.2 |
| 2.6 | N-{2-[4-(3-Dimethylamino-propyl)-piperazin-1-yl]-2-oxo-ethyl}-4-(2-phenoxy-phenylsulfamoyl)-benzamide | 580.2 |
| 2.7 | N-{2-Oxo-2-[4-(2-pyrrolidin-1-yl-ethyl)-piperidin-1-yl]-ethyl}-4-(2-phenoxy-phenylsulfamoyl)-benzamide | 591.2 |
| 2.8 | N-(2-[1,4']Bipiperidinyl-1'-yl-2-oxo-ethyl)-4-(2-phenoxy-phenylsulfamoyl)-benzamide | 577.2 |
| 2.9 | N-[2-Oxo-2-(4-pyrrolidin-1-yl-piperidin-1-yl)-ethyl]-4-(2-phenoxy-phenylsulfamoyl)-benzamide | 563.2 |
| 2.10 | N-[2-(4-Hydroxy-piperidin-1-yl)-2-oxo-ethyl]-4-(2-phenoxy-phenylsulfamoyl)-benzamide | 510.2 |
| 2.11 | N-(2-{4-[2-(2-Hydroxy-ethoxy)-ethyl]-piperazin-1-yl}-2-oxo-ethyl)-4-(2-phenoxy-phenylsulfamoyl)-benzamide | 583.2 |
| 2.12 | N-[2-Oxo-2-(4-phenyl-piperazin-1-yl)-ethyl]-4-(2-phenoxy-phenylsulfamoyl)-benzamide | 571.2 |
| 2.13 | N-(2-Oxo-2-piperidin-1-yl-ethyl)-4-(2-phenoxy-phenylsulfamoyl)-benzamide | 494.2 |
| 2.14 | N-{2-[4-(4-Methyl-piperazine-1-carbonyl)-piperidin-1-yl]-2-oxo-ethyl}-4-(2-phenoxy-phenylsulfamoyl)-benzamide | 620.2 |
| 2.15 | 1-{2-[4-(2-Phenoxy-phenylsulfamoyl)-benzoylamino]-acetyl}-piperidine-4-carboxylic acid amide | 537.2 |
| 2.16 | N-[2-(2-Hydroxymethyl-piperidin-1-yl)-2-oxo-ethyl]-4-(2-phenoxy-phenylsulfamoyl)-benzamide | 524.2 |

TABLE 2-continued

| Example | Name | MS (EI) (MH$^+$) |
|---|---|---|
| 2.17 | N-[2-(3-Hydroxy-piperidin-1-yl)-2-oxo-ethyl]-4-(2-phenoxy-phenylsulfamoyl)-benzamide | 510.2 |
| 2.18 | N-{2-[2-(2-Hydroxy-ethyl)-piperidin-1-yl]-2-oxo-ethyl}-4-(2-phenoxy-phenylsulfamoyl)-benzamide | 538.2 |
| 2.19 | N-[2-Oxo-2-(4-oxo-piperidin-1-yl)-ethyl]-4-(2-phenoxy-phenylsulfamoyl)-benzamide | 508.2 |
| 2.20 | N-[2-(3-Hydroxymethyl-piperidin-1-yl)-2-oxo-ethyl]-4-(2-phenoxy-phenylsulfamoyl)-benzamide | 524.2 |
| 2.21 | N-[2-Oxo-2-(3-oxo-piperazin-1-yl)-ethyl]-4-(2-phenoxy-phenylsulfamoyl)-benzamide | 509.2 |
| 2.22 | N-[2-(4-Hydroxymethyl-piperidin-1-yl)-2-oxo-ethyl]-4-(2-phenoxy-phenylsulfamoyl)-benzamide | 524.2 |
| 2.23 | N-{2-[4-(2-Hydroxy-ethyl)-piperidin-1-yl]-2-oxo-ethyl}-4-(2-phenoxy-phenylsulfamoyl)-benzamide | 538.2 |
| 2.24 | N-(2-Azepan-1-yl-2-oxo-ethyl)-4-(2-phenoxy-phenylsulfamoyl)-benzamide | 508.2 |
| 2.25 | N-(2-Oxo-2-pyrrolidin-1-yl-ethyl)-4-(2-phenoxy-phenylsulfamoyl)-benzamide | 480.2 |
| 2.26 | N-[2-(3-Hydroxy-pyrrolidin-1-yl)-2-oxo-ethyl]-4-(2-phenoxy-phenylsulfamoyl)-benzamide | 496.2 |
| 2.27 | N-(2-Oxo-2-thiomorpholin-4-yl-ethyl)-4-(2-phenoxy-phenylsulfamoyl)-benzamide | 512.2 |
| 2.28 | N-[2-(1,1-Dioxo-1λ$^6$-thiomorpholin-4-yl)-2-oxo-ethyl]-4-(2-phenoxy-phenylsulfamoyl)-benzamide | 544.1 |
| 2.29 | N-[2-(4-Cyano-piperidin-1-yl)-2-oxo-ethyl]-4-(2-phenoxy-phenylsulfamoyl)-benzamide | 519.2 |
| 2.30 | N-[2-(4-Acetyl-piperazin-1-yl)-2-oxo-ethyl]-4-(2-phenoxy-phenylsulfamoyl)-benzamide | 537.2 |
| 2.31 | N-{2-Oxo-2-[4-(tetrahydro-furan-2-carbonyl)-piperazin-1-yl]-ethyl}-4-(2-phenoxy-phenylsulfamoyl)-benzamide | 593.2 |
| 2.32 | N-{2-[4-(3-Hydroxy-phenyl)-piperazin-1-yl]-2-oxo-ethyl}-4-(2-phenoxy-phenylsulfamoyl)-benzamide | 587.2 |
| 2.33 | N-{2-[4-(4-Hydroxy-phenyl)-piperazin-1-yl]-2-oxo-ethyl}-4-(2-phenoxy-phenylsulfamoyl)-benzamide | 587.2 |
| 2.34 | N-{2-[4-(1-Methyl-piperidin-4-yl)-piperazin-1-yl]-2-oxo-ethyl}-4-(2-phenoxy-phenylsulfamoyl)-benzamide | 592.1 |
| 2.35 | N-[2-(4-Morpholin-4-yl-piperidin-1-yl)-2-oxo-ethyl]-4-(2-phenoxy-phenylsulfamoyl)-benzamide | 579.2 |
| 2.36 | N-[2-(4-Ethyl-piperazin-1-yl)-2-oxo-ethyl]-4-(2-phenoxy-phenylsulfamoyl)-benzamide | 523.2 |
| 2.37 | N-[2-Oxo-2-(4-phenyl-piperidin-1-yl)-ethyl]-4-(2-phenoxy-phenylsulfamoyl)-benzamide | 570.2 |
| 2.38 | N-[2-(4-Benzoyl-piperazin-1-yl)-2-oxo-ethyl]-4-(2-phenoxy-phenylsulfamoyl)-benzamide | 599.2 |
| 2.39 | N-{2-[4-(Furan-2-carbonyl)-piperazin-1-yl]-2-oxo-ethyl}-4-(2-phenoxy-phenylsulfamoyl)-benzamide | 589.2 |
| 2.40 | N-{2-[4-(2-Fluoro-phenyl)-piperazin-1-yl]-2-oxo-ethyl}-4-(2-phenoxy-phenylsulfamoyl)-benzamide | 589.2 |
| 2.41 | N-{2-[4-(4-Fluoro-phenyl)-piperazin-1-yl]-2-oxo-ethyl}-4-(2-phenoxy-phenylsulfamoyl)-benzamide | 589.2 |
| 2.42 | N-[2-Oxo-2-(4-phenethyl-piperazin-1-yl)-ethyl]-4-(2-phenoxy-phenylsulfamoyl)-benzamide | 599.2 |
| 2.43 | N-[2-(4-Cyclopropylmethyl-piperazin-1-yl)-2-oxo-ethyl]-4-(2-phenoxy-phenylsulfamoyl)-benzamide | 549.2 |
| 2.44 | N-{2-Oxo-2-[4-(tetrahydro-furan-2-ylmethyl)-piperazin-1-yl]-ethyl}-4-(2-phenoxy-phenylsulfamoyl)-benzamide | 579.2 |
| 2.45 | N-[2-(4-Cyclohexyl-piperazin-1-yl)-2-oxo-ethyl]-4-(2-phenoxy-phenylsulfamoyl)-benzamide | 577.2 |
| 2.46 | N-{2-[4-(4-Cyano-phenyl)-piperazin-1-yl]-2-oxo-ethyl}-4-(2-phenoxy-phenylsulfamoyl)-benzamide | 596.2 |
| 2.47 | N-[2-(4-Ethanesulfonyl-piperazin-1-yl)-2-oxo-ethyl]-4-(2-phenoxy-phenylsulfamoyl)-benzamide | 587.2 |
| 2.48 | N-{2-[4-(2-Cyano-phenyl)-piperazin-1-yl]-2-oxo-ethyl}-4-(2-phenoxy-phenylsulfamoyl)-benzamide | 596.2 |
| 2.49 | N-[2-(4-Cyclohexylmethyl-piperazin-1-yl)-2-oxo-ethyl]-4-(2-phenoxy-phenylsulfamoyl)-benzamide | 591.2 |
| 2.50 | N-[2-(Octahydro-isoquinolin-2-yl)-2-oxo-ethyl]-4-(2-phenoxy-phenylsulfamoyl)-benzamide | 548.2 |
| 2.51 | (1-{2-[4-(2-Phenoxy-phenylsulfamoyl)-benzoylamino]-acetyl}-piperidin-4-yl)-acetic acid methyl ester | 566.2 |
| 2.52 | N-{2-Oxo-2-[4-(3-piperidin-4-yl-propyl)-piperidin-1-yl]-ethyl}-4-(2-phenoxy-phenylsulfamoyl)-benzamide | 619.3 |
| 2.53 | N-[2-(4-Cyanomethyl-piperidin-1-yl)-2-oxo-ethyl]-4-(2-phenoxy-phenylsulfamoyl)-benzamide | 533.2 |
| 2.54 | N-(2-Morpholin-4-yl-2-oxo-ethyl)-4-(2-phenoxy-phenylsulfamoyl)-benzamide | 496.1 |

TABLE 2-continued

| Example | Name | MS (EI) (MH+) |
|---|---|---|
| 2.55 | N-[2-(4,4-Difluoro-piperidin-1-yl)-2-oxo-ethyl]-4-(2-phenoxy-phenylsulfamoyl)-benzamide | 530.2 |
| 2.56 | N-[2-(4-Methyl-piperidin-1-yl)-2-oxo-ethyl]-4-(2-phenoxy-phenylsulfamoyl)-benzamide | 508.2 |
| 2.57 | 1-{2-[4-(2-Phenoxy-phenylsulfamoyl)-benzoylamino]-acetyl}-piperidine-4-carboxylic acid (2-hydroxy-ethyl)-amide | 581.2 |
| 2.58 | N-[2-(4-Acetylamino-piperidin-1-yl)-2-oxo-ethyl]-4-(2-phenoxy-phenylsulfamoyl)-benzamide | 551.2 |
| 2.59 | N-[2-(4-Methanesulfonylamino-piperidin-1-yl)-2-oxo-ethyl]-4-(2-phenoxy-phenylsulfamoyl)-benzamide | 587.2 |
| 2.60 | 1-{2-[4-(2-Phenoxy-phenylsulfamoyl)-benzoylamino]-acetyl}-piperidine-4-carboxylic acid cycloheptylamide | 633.2 |
| 2.61 | N-[2-((S)-5-Benzyl-2,5-diaza-bicyclo[2.2.1]hept-2-yl)-2-oxo-ethyl]-4-(2-phenoxy-phenylsulfamoyl)-benzamide | 597.2 |
| 2.62 | 1-{2-[4-(2-Phenoxy-phenylsulfamoyl)-benzoylamino]-acetyl}-piperidine-4-carboxylic acid dimethylamid | 565.4 |
| 2.63 | N-[2-(4-Methoxy-piperidin-1-yl)-2-oxo-ethyl]-4-(2-phenoxy-phenylsulfamoyl)-benzamide | 524.4 |
| 2.64 | 1-{2-[4-(2-Phenoxy-phenylsulfamoyl)-benzoylamino]-acetyl}-piperidine-4-carboxylic acid tert-butylamide | 593.4 |
| 2.65 | N-(2-Azocan-1-yl-2-oxo-ethyl)-4-(2-phenoxy-phenylsulfamoyl)-benzamide | 522.4 |

Example 3.1

4-(2-Benzoyl-phenylsulfamoyl)-N-{2-oxo-2-[4-(2-pyrrolidin-1-yl-ethyl)-piperazin-1-yl]-ethyl}-benzamide a) 4-(2-Benzoyl-phenylsulfamoyl)-benzoic acid The title compound was prepared from 2-amino-benzophenone according to the method described in Example 1.1/c. MS (EI) 382.2 (MH+).

b) [4-(2-Benzoyl-phenylsulfamoyl)-benzoylamino]-acetic acid ethyl ester

The title compound was prepared from 4-(2-benzoyl-phenylsulfamoyl)-benzoic acid and glycine ethyl ester hydrochloride (Aldrich) according to the method described in Example 1.1/d. MS (EI) 867.2 (MH+).

c) [4-(2-Benzoyl-phenylsulfamoyl)-benzoylamino]-acetic acid

The title compound was prepared from [4-(2-benzoyl-phenylsulfamoyl)-benzoylamino]-acetic acid ethyl ester according to the method described in Example 1.1/e. MS (EI) 439.2 (MH+).

d) 4-(2-Benzoyl-phenylsulfamoyl)-N-{2-oxo-2-[4-(2-pyrrolidin-1-yl-ethyl)-piperazin-1-yl]-ethyl}-benzamide The title compound was prepared from [4-(2-benzoyl-phenylsulfamoyl)-benzoylamino]-acetic acid and 1-(2-pyrrolidin-1-yl-ethyl)-piperazine (EMKA-Chemie) according to the method described in Example 1.1/f. MS (EI) 604.2 (MH+). Compounds of Table 3 were prepared from [4-(2-benzoyl-phenylsulfamoyl)-benzoylamino]-acetic acid (Example 3.1/c) according to the method described in Example 1.1/f.

TABLE 3

| Example | Name | MS (EI) (MH+) |
|---|---|---|
| 3.2 | 4-(2-Benzoyl-phenylsulfamoyl)-N-{2-[4-(2-dimethylamino-ethyl)-piperazin-1-yl]-2-oxo-ethyl}-benzamide | 578.2 |
| 3.3 | 4-(2-Benzoyl-phenylsulfamoyl)-N-(2-oxo-2-piperidin-1-yl-ethyl)-benzamide | 506.2 |
| 3.4 | N-(2-Azepan-1-yl-2-oxo-ethyl)-4-(2-benzoyl-phenylsulfamoyl)-benzamide | 520.2 |
| 3.5 | 4-(2-Benzoyl-phenylsulfamoyl)-N-[2-(4-cyano-piperidin-1-yl)-2-oxo-ethyl]-benzamide | 531.2 |
| 3.6 | 4-(2-Benzoyl-phenylsulfamoyl)-N-[2-oxo-2-(4-trifluoromethyl-piperidin-1-yl)-ethyl]-benzamide | 574.2 |
| 3.7 | 4-(2-Benzoyl-phenylsulfamoyl)-N-[2-(4-methyl-piperidin-1-yl)-2-oxo-ethyl]-benzamide | 520.2 |
| 3.8 | 4-(2-Benzoyl-phenylsulfamoyl)-N-{2-[4-(1-methyl-piperidin-3-ylmethyl)-piperazin-1-yl]-2-oxo-ethyl}-benzamide | 618.2 |
| 3.9 | 4-(2-Benzoyl-phenylsulfamoyl)-N-[2-(4-hydroxymethyl-piperidin-1-yl)-2-oxo-ethyl]-benzamide | 536.2 |
| 3.10 | 4-(2-Benzoyl-phenylsulfamoyl)-N-{2-[4-(2-hydroxy-ethyl)-piperidin-1-yl]-2-oxo-ethyl}-benzamide | 550.2 |
| 3.11 | 4-(2-Benzoyl-phenylsulfamoyl)-N-(2-oxo-2-pyrrolidin-1-yl-ethyl)-benzamide | 492.2 |
| 3.12 | 4-(2-Benzoyl-phenylsulfamoyl)-N-[2-(3-hydroxy-pyrrolidin-1-yl)-2-oxo-ethyl]-benzamide | 508.2 |

TABLE 3-continued

| Example | Name | MS (EI) (MH+) |
|---|---|---|
| 3.13 | 4-(2-Benzoyl-phenylsulfamoyl)-N-{2-oxo-2-[4-(3-pyrrolidin-1-yl-propyl)-piperazin-1-yl]-ethyl}-benzamide | 618.2 |
| 3.14 | 4-(2-Benzoyl-phenylsulfamoyl)-N-{2-[4-(3-dimethylamino-propyl)-piperazin-1-yl]-2-oxo-ethyl}-benzamide | 592.2 |
| 3.15 | 4-(2-Benzoyl-phenylsulfamoyl)-N-{2-oxo-2-[4-(2-pyrrolidin-1-yl-ethyl)-piperidin-1-yl]-ethyl}-benzamide | 603.2 |
| 3.16 | 4-(2-Benzoyl-phenylsulfamoyl)-N-[2-(4-hydroxy-piperidin-1-yl)-2-oxo-ethyl]-benzamide | 522.2 |
| 3.17 | 1-{2-[4-(2-Benzoyl-phenylsulfamoyl)-benzoylamino]-acetyl}-piperidine-4-carboxylic acid amide | 549.2 |
| 3.18 | 4-(2-Benzoyl-phenylsulfamoyl)-N-(2-morpholin-4-yl-2-oxo-ethyl)-benzamide | 508.2 |
| 3.19 | 4-(2-Benzoyl-phenylsulfamoyl)-N-[2-oxo-2-(3-oxo-piperazin-1-yl)-ethyl]-benzamide | 521.2 |
| 3.20 | 4-(2-Benzoyl-phenylsulfamoyl)-N-(2-oxo-2-thiomorpholin-4-yl-ethyl)-benzamide | 524.2 |
| 3.21 | 4-(2-Benzoyl-phenylsulfamoyl)-N-[2-(1,1-dioxo-1$\lambda^6$-thiomorpholin-4-yl)-2-oxo-ethyl]-benzamide | 556.1 |
| 3.22 | 4-(2-Benzoyl-phenylsulfamoyl)-N-[2-(3-hydroxymethyl-piperidin-1-yl)-2-oxo-ethyl]-benzamide | 536.2 |
| 3.23 | 4-(2-Benzoyl-phenylsulfamoyl)-N-{2-oxo-2-[4-(3-pyrrolidin-1-yl-propyl)-[1,4]diazepan-1-yl]-ethyl}-benzamide | 632.5 |
| 3.24 | 4-(2-Benzoyl-phenylsulfamoyl)-N-[2-oxo-2-(4-oxo-piperidin-1-yl)-ethyl]-benzamide | 520.3 |

Example 4.1

4-[5-Fluoro-2-(4-fluoro-phenoxy)-phenylsulfamoyl]-N-(2-oxo-2-piperidin-1-yl-ethyl)-benzamide a) 4-[5-Fluoro-2-(4-fluoro-phenoxy)-phenylsulfamoyl]-benzoic acid The title compound was prepared from 5-fluoro-2-(4-fluoro-phenoxy)-phenylamine [*Yakugaku Zasshi;* 88 (1968) 1361, 1365; *Chem. Abstr.;* 70 (1969) 68312] according to the method described in Example 1.1/c. MS (EI) 406.3 (MH+).

b) {4-[5-Fluoro-2-(4-fluoro-phenoxy)-phenylsulfamoyl]-benzoylamino}-acetic acid ethyl ester The title compound was prepared from 4-[5-fluoro-2-(4-fluoro-phenoxy)-phenylsulfamoyl]-benzoic acid and glycine ethyl ester hydrochloride (Aldrich) according to the method described in Example 1.1/d.

c) {4-[5-Fluoro-2-(4-fluoro-phenoxy)-phenylsulfamoyl]-benzoylamino}-acetic acid

The title compound was prepared from {4-[5-fluoro-2-(4-fluoro-phenoxy)-phenylsulfamoyl]-benzoylamino}-acetic acid ethyl ester according to the method described in Example 1.1/e. MS (EI) 463.1 (MH+).

d) 4-[5-Fluoro-2-(4-fluoro-phenoxy)-phenylsulfamoyl]-N-(2-oxo-2-piperidin-1-yl-ethyl)-benzamide The title compound was prepared from {4-[5-fluoro-2-(4-fluoro-phenoxy)-phenylsulfamoyl]-benzoylamino}-acetic acid and piperidine according to the method described in Example 1.1/f. MS (EI) 533.3 (MH+).

Compounds of Table 4 were prepared from {4-[5-fluoro-2-(4-fluoro-phenoxy)-phenylsulfamoyl]-benzoylamino}-acetic acid (Example 4.1/c) according to the method described in Example 1.1/f.

TABLE 4

| Example | Name | MS (EI) (MH+) |
|---|---|---|
| 4.2 | N-(2-Azepan-1-yl-2-oxo-ethyl)-4-[5-fluoro-2-(4-fluoro-phenoxy)-phenylsulfamoyl]-benzamide | 544.4 |
| 4.3 | 4-[5-Fluoro-2-(4-fluoro-phenoxy)-phenylsulfamoyl]-N-[2-(4-hydroxy-piperidin-1-yl)-2-oxo-ethyl]-benzamide | 546.3 |
| 4.4 | 4-[5-Fluoro-2-(4-fluoro-phenoxy)-phenylsulfamoyl]-N-[2-(4-hydroxymethyl-piperidin-1-yl)-2-oxo-ethyl]-benzamide | 560.3 |
| 4.5 | 4-[5-Fluoro-2-(4-fluoro-phenoxy)-phenylsulfamoyl]-N-{2-[4-(2-hydroxy-ethyl)-piperidin-1-yl]-2-oxo-ethyl}-benzamide | 574.4 |
| 4.6 | 4-[5-Fluoro-2-(4-fluoro-phenoxy)-phenylsulfamoyl]-N-[2-oxo-2-(4-phenyl-piperazin-1-yl)-ethyl]-benzamide | 607.4 |
| 4.7 | 4-[5-Fluoro-2-(4-fluoro-phenoxy)-phenylsulfamoyl]-N-{2-oxo-2-[4-(2-pyrrolidin-1-yl-ethyl)-piperidin-1-yl]-ethyl}-benzamide | 627.5 |

Example 5.1

4-[2-(2-Chloro-4-fluoro-phenoxy)-phenylsulfamoyl]-N-[2-(4-hydroxy-piperidin-1-yl)-2-oxo-ethyl]-benzamide a) 2-Chloro-4-fluoro-1-(2-nitro-phenoxy)-benzene The title compound was prepared from 2-chloro-4-fluoro-phenol according to the method described in Example 1.1/a.

b) 2-(2-Chloro-4-fluoro-phenoxy)-phenylamine

The title compound was prepared from 2-chloro-4-fluoro-1-(2-nitro-phenoxy)-benzene according to the method described in Example 1.1/b.

c) 4-[2-(2-Chloro-4-fluoro-phenoxy)-phenylsulfamoyl]-benzoic acid

The title compound was prepared from 2-(2-chloro-4-fluoro-phenoxy)-phenylamine according to the method described in Example 1.1/c. MS (EI) 422.1 (MH$^+$).

d) {4-[2-(2-Chloro-4-fluoro-phenoxy)-phenylsulfamoyl]-benzoylamino}-acetic acid ethyl ester The title compound was prepared from 4-[2-(2-chloro-4-fluoro-phenoxy)-phenylsulfamoyl]-benzoic acid and glycine ethyl ester hydrochloride according to the method described in Example 1.1/d.

e) {4-[2-(2-Chloro-4-fluoro-phenoxy)-phenylsulfamoyl]-benzoylamino}-acetic acid

The title compound was prepared from {4-[2-(2-chloro-4-fluoro-phenoxy)-phenylsulfamoyl]-benzoylamino}-acetic acid ethyl ester according to the method described in Example 1.1/e. MS (EI) 479 (MH$^+$).

f) 4-[2-(2-Chloro-4-fluoro-phenoxy)-phenylsulfamoyl]-N-[2-(4-hydroxy-piperidin-1-yl)-2-oxo-ethyl]-benzamide The title compound was prepared from {4-[2-(2-chloro-4-fluoro-phenoxy)-phenylsulfamoyl]-benzoylamino}-acetic acid and 4-hydroxypiperidine according to the method described in Example 1.1/f. MS (EI) 562.3 (MH$^+$).
Compounds of Table 5 were prepared from {4-[2-(2-chloro-4-fluoro-phenoxy)-phenylsulfamoyl]-benzoylamino}-acetic acid (Example 5.1/e) according to the method described in Example 1.1/f.

Example 6.1

4-[2-(2,4-Dichloro-benzoyl)-phenylsulfamoyl]-N-{2-oxo-2-[4-(2-pyrrolidin-1-yl-ethyl)-piperazin-1-yl]-ethyl}-benzamide a) 4-[2-(2,4-Dichloro-benzoyl)-phenylsulfamoyl]-benzoic acid The title compound was prepared from (2-amino-phenyl)-(2,4-dichloro-phenyl)-methanone [*Synthesis*, (1980) 677-688] and 4-chlorosulfonyl-benzoic acid according to the method described in Example 1.1/c. MS (EI) 451 (MH$^+$).

b) {4-[2-(2,4-Dichloro-benzoyl)-phenylsulfamoyl]-benzoylamino}-acetic acid ethyl ester The title compound was prepared from 4-[2-(2,4-dichloro-benzoyl)-phenylsulfamoyl]-benzoic acid and glycine ethyl ester hydrochloride according to the method described in Example 1.1/d. MS (EI) 536.1 (MH$^+$).

c) {4-[2-(2,4-Dichloro-benzoyl)-phenylsulfamoyl]-benzoylamino}-acetic acid

The title compound was prepared from {4-[2-(2,4-dichloro-benzoyl)-phenylsulfamoyl]-benzoylamino}-acetic acid ethyl ester according to the method described in Example 1.1/e. MS (EI) 508 (MH$^+$).

d) 4-[2-(2,4-Dichloro-benzoyl)-phenylsulfamoyl]-N-{2-oxo-2-[4-(2-pyrrolidin-1-yl-ethyl)-piperazin-1-yl]-ethyl}-benzamide The title compound was prepared from {4-[2-(2,4-dichloro-benzoyl)-phenylsulfamoyl]-benzoylamino}-acetic acid and 1-(2-pyrrolidin-1-yl-ethyl)-piperazine (EMKA-Chemie) according to the method described in Example 1.1/f. MS (EI) 673.2 (MH$^+$).

Compounds of Table 6 were prepared from {4-[2-(2,4-dichloro-benzoyl)-phenylsulfamoyl]-benzoylamino}-acetic acid (Example 6.1/c) according to the method described in Example 1.1/f.

TABLE 5

| Example | Name | MS (EI) (MH$^+$) |
| --- | --- | --- |
| 5.2 | 4-[2-(2-Chloro-4-fluoro-phenoxy)-phenylsulfamoyl]-N-{2-oxo-2-[4-(2-pyrrolidin-1-yl-ethyl)-piperazin-1-yl]-ethyl}-benzamide | 644.4 |
| 5.3 | 4-[2-(2-Chloro-4-fluoro-phenoxy)-phenylsulfamoyl]-N-{2-oxo-2-[4-(3-pyrrolidin-1-yl-propyl)-piperazin-1-yl]-ethyl}-benzamide | 658.5 |
| 5.4 | 4-[2-(2-Chloro-4-fluoro-phenoxy)-phenylsulfamoyl]-N-{2-oxo-2-[4-(2-pyrrolidin-1-yl-ethyl)-piperidin-1-yl]-ethyl}-benzamide | 643.4 |
| 5.5 | 4-[2-(2-Chloro-4-fluoro-phenoxy)-phenylsulfamoyl]-N-[2-(4-hydroxymethyl-piperidin-1-yl)-2-oxo-ethyl]-benzamide | 576.3 |
| 5.6 | 1-(2-{4-[2-(2-Chloro-4-fluoro-phenoxy)-phenylsulfamoyl]-benzoylamino}-acetyl)-piperidine-4-carboxylic acid amide | 589.3 |
| 5.7 | 4-[2-(2-Chloro-4-fluoro-phenoxy)-phenylsulfamoyl]-N-{2-[4-(1-methyl-piperidin-4-yl)-piperazin-1-yl]-2-oxo-ethyl}-benzamide | 644.4 |

TABLE 6

| Example | Name | MS (EI) (MH+) |
|---|---|---|
| 6.2 | 4-[2-(2,4-Dichloro-benzoyl)-phenylsulfamoyl]-N-{2-oxo-2-[4-(3-piperidin-1-yl-propyl)-piperazin-1-yl]-ethyl}-benzamide | 701.4 |
| 6.3 | 4-[2-(2,4-Dichloro-benzoyl)-phenylsulfamoyl]-N-{2-oxo-2-[4-(3-pyrrolidin-1-yl-propyl)-piperazin-1-yl]-ethyl}-benzamide | 687.2 |
| 6.4 | 4-[2-(2,4-Dichloro-benzoyl)-phenylsulfamoyl]-N-{2-[4-(3-dimethylamino-propyl)-piperazin-1-yl]-2-oxo-ethyl}-benzamide | 661.4 |
| 6.5 | 4-[2-(2,4-Dichloro-benzoyl)-phenylsulfamoyl]-N-{2-oxo-2-[4-(2-pyrrolidin-1-yl-ethyl)-piperidin-1-yl]-ethyl}-benzamide | 672.4 |
| 6.6 | 4-[2-(2,4-Dichloro-benzoyl)-phenylsulfamoyl]-N-[2-(4-hydroxy-piperidin-1-yl)-2-oxo-ethyl]-benzamide | 591.2 |
| 6.7 | 4-[2-(2,4-Dichloro-benzoyl)-phenylsulfamoyl]-N-[2-(4-hydroxymethyl-piperidin-1-yl)-2-oxo-ethyl]-benzamide | 605.2 |
| 6.8 | 1-(2-{4-[2-(2,4-Dichloro-benzoyl)-phenylsulfamoyl]-benzoylamino}-acetyl)-piperidine-4-carboxylic acid amide | 618.3 |
| 6.9 | 4-[2-(2,4-Dichloro-benzoyl)-phenylsulfamoyl]-N-{2-[4-(1-methyl-piperidin-4-yl)-piperazin-1-yl]-2-oxo-ethyl}-benzamide | 673.4 |

Example 7.1

4-[2-(4-Fluoro-phenoxy)-phenylsulfamoyl]-N-[2-(4-hydroxy-piperidin-1-yl)-2-oxo-ethyl]-benzamide a)
4-[2-(4-Fluoro-phenoxy)-phenylsulfamoyl]-benzoic acid The title compound was prepared from 2-(4-fluoro-phenoxy)-phenylamine [*Helv. Chim. Acta;* 48 (1965) 336-347] according to the method described in Example 1.1/c. MS (EI) 388.2 (MH+).

b) {4-[2-(4-Fluoro-phenoxy)-phenylsulfamoyl]-benzoylamino}-acetic acid ethyl ester The title compound was prepared from 4-[2-(4-fluoro-phenoxy)-phenylsulfamoyl]-benzoic acid and glycine ethyl ester hydrochloride according to the method described in Example 1.1/d.

c) {4-[2-(4-Fluoro-phenoxy)-phenylsulfamoyl]-benzoylamino}-acetic acid

The title compound was prepared from {4-[2-(4-fluoro-phenoxy)-phenylsulfamoyl]-benzoylamino}-acetic acid ethyl ester according to the method described in Example 1.1/e. MS (EI) 445.1 (MH+).

d) 4-[2-(4-Fluoro-phenoxy)-phenylsulfamoyl]-N-[2-(4-hydroxy-piperidin-1-yl)-2-oxo-ethyl]-benzamide The title compound was prepared from {4-[2-(4-fluoro-phenoxy)-phenylsulfamoyl]-benzoylamino}-acetic acid and 4-hydroxypiperidine according to the method described in Example 1.1/f. MS (EI) 528.4 (MH+).
Compounds of Table 7 were prepared from {4-[2-(4-fluoro-phenoxy)-phenylsulfamoyl]benzoylamino}-acetic acid (Example 7.1/c) according to the method described in Example 1.1/f.

TABLE 7

| Example | Name | MS (EI) (MH+) |
|---|---|---|
| 7.2 | 4-[2-(4-Fluoro-phenoxy)-phenylsulfamoyl]-N-(2-oxo-2-piperidin-1-yl-ethyl)-benzamide | 512.3 |
| 7.3 | 4-[2-(4-Fluoro-phenoxy)-phenylsulfamoyl]-N-[2-(4-hydroxymethyl-piperidin-1-yl)-2-oxo-ethyl]-benzamide | 542.4 |
| 7.4 | 4-[2-(4-Fluoro-phenoxy)-phenylsulfamoyl]-N-{2-[4-(2-hydroxy-ethyl)-piperidin-1-yl]-2-oxo-ethyl}-benzamide | 556.2 |

Example 8.1

N-[2-(4-Hydroxy-piperidin-1-yl)-2-oxo-ethyl]-4-[2-(4-trifluoromethyl-phenoxy)-phenylsulfamoyl]-benzamide a) 4-[2-(4-Trifluormethyl-phenoxy)-phenylsulfamoyl]-benzoic acid The title compound was prepared from 2-(4-trifluoromethyl-phenoxy)-phenylamine [*J. Chem. Soc. Perkin Trans.* 1. (1976) 1279-1285] according to the method described in Example 1.1/c. MS (EI) 438.0 (MH+).

b) {4-[2-(4-Trifluormethyl-phenoxy)-phenylsulfamoyl]-benzoylamino}-acetic acid ethyl ester The title compound was prepared from 4-[2-(4-trifluoromethyl-phenoxy)-phenylsulfamoyl]-benzoic acid and glycine ethyl ester hydrochloride according to the method described in Example 1.1/d.

c) {4-[2-(4-Trifluoromethyl-phenoxy)-phenylsulfamoyl]-benzoylamino}-acetic acid

The title compound was prepared from {4-[2-(4-trifluoromethyl-phenoxy)-phenylsulfamoyl]-benzoylamino}-acetic acid ethyl ester according to the method described in Example 1.1/e. MS (EI) 475.2 (MH+).

d) N-[2-(4-Hydroxy-piperidin-1-yl)-2-oxo-ethyl]-4-[2-(4-trifluoromethyl-phenoxy)-phenylsulfamoyl]-benzamide The title compound was prepared from {4-[2-(4-trifuormethyl-phenoxy)-phenylsulfamoyl]-benzoylamino}-acetic acid and 4-hydroxypiperidine according to the method described in Example 1.1/f. MS (EI) 578.3 (MH⁺).

Example 9.1

N-[2-(4-Hydroxy-piperidin-1-yl)-2-oxo-ethyl]-4-[2-(4-trifluoromethoxy-phenoxy)-phenylsulfamoyl]-benzamide a) 4-[2-(4-Trifluormethoxy-phenoxy)-phenylsulfamoyl]-benzoic acid The title compound was prepared from 2-(4-trifluoromethoxy-phenoxy)-phenylamine [*J. Med. Chem.* 13 (1970) 295-297] according to method described in Example 1.1/c. MS (EI) 454.1 (MH⁺).

b) {4-[2-(4-Trifluormethoxy-phenoxy)-phenylsulfamoyl]-benzoylamino}-acetic acid ethyl ester The title compound was prepared from 4-[2-(4-trifluoromethoxy-phenoxy)-phenylsulfamoyl]-benzoic acid and glycine ethyl ester hydrochloride according to the method described in Example 1.1/d.

c) {4-[2-(4-Trifluoromethoxy-phenoxy)-phenylsulfamoyl]-benzoylamino}-acetic acid The title compound was prepared from {4-[2-(4-trifluoromethoxy-phenoxy)-phenylsulfamoyl]-benzoylamino}-acetic acid ethyl ester according to the method described in Example 1.1/e. MS (EI) 511 (MH⁺).

d) N-[2-(4-Hydroxy-piperidin-1-yl)-2-oxo-ethyl]-4-[2-(4-trifluoromethoxy-phenoxy)-phenylsulfamoyl]-benzamide The title compound was prepared from {4-[2-(4-trifuormethoxy-phenoxy)-phenylsulfamoyl]-benzoylamino}-acetic acid and 4-hydroxypiperidine according to the method described in Example 1.1/f. MS (EI) 594.3 (MH⁺).
Compounds of Table 9 were prepared from {4-[2-(4-trifluoromethoxy-phenoxy)-phenylsulfamoyl]-benzoylamino}-acetic acid (Example 9.1/c) according to the method described in Example 1.1/f.

TABLE 9

| Example | Name | MS (EI) (MH⁺) |
|---|---|---|
| 9.2 | N-{2-Oxo-2-[4-(2-pyrrolidin-1-yl-ethyl)-piperazin-1-yl]-ethyl}-4-[2-(4-trifluoromethoxy-phenoxy)-phenylsulfamoyl]-benzamide | 676.5 |
| 9.3 | N-{2-[4-(1-Methyl-piperidin-4-yl)-piperazin-1-yl]-2-oxo-ethyl}-4-[2-(4-trifluoromethoxy-phenoxy)-phenylsulfamoyl]-benzamide | 676.5 |

Example 10.1

4-[2-(4-Bromo-2-chloro-phenoxy)-phenylsulfamoyl]-N-[2-(4-hydroxy-piperidin-1-yl)-2-oxo-ethyl]-benzamide a) 4-Bromo-2-chloro-1-(2-nitro-phenoxy)-benzene The title compound was prepared from 4-bromo-2-chlorophenol according to the method described in Example 1.1/a. MS (EI) 329.3 (MH⁺).

b) 2-(4-Bromo-2-chloro-phenoxy)-phenylamine

The title compound was prepared from 4-bromo-2-chloro-1-(2-nitro-phenoxy)-benzene according to the method described in Example 1.1/b. MS (EI) 300.2 (MH⁺).

c) 4-[2-(4-Bromo-2-chloro-phenoxy)-phenylsulfamoyl]-benzoic acid

The title compound was prepared from 2-(4-bromo-2-chloro-phenoxy)-phenylamine according to the method described in Example 1.1/c. MS (EI) 483.4 (MH⁺).

d) {4-[2-(4-Bromo-2-chloro-phenoxy)-phenylsulfamoyl]-benzoylamino}-acetic acid ethyl ester The title compound was prepared from 4-[2-(4-bromo-2-chloro-phenoxy)-phenylsulfamoyl]-benzoic acid and glycine ethyl ester hydrochloride according to the method described in Example 1.1/d.

e) {4-[2-(4-Bromo-2-chloro-phenoxy)-phenylsulfamoyl]-benzoylamino}-acetic acid

The title compound was prepared from {4-[2-(4-bromo-2-chloro-phenoxy)-phenylsulfamoyl]-benzoylamino}-acetic acid ethyl ester according to the method described in Example 1.1/e. MS (EI) 541.1 (MH⁺).

f) 4-[2-(4-Bromo-2-chloro-phenoxy)-phenylsulfamoyl]-N-[2-(4-hydroxy-piperidin-1-yl)-2-oxo-ethyl]-benzamide The title compound was prepared from {4-[2-(4-bromo-2-chloro-phenoxy)-phenylsulfamoyl]-benzoylamino}-acetic acid and 4-hydroxypiperidine according to the method described in Example 1.1/f. MS (EI) 623.3 (MH⁺).
Compounds of Table 10 were prepared from {4-[2-(4-bromo-2-chloro-phenoxy)-phenylsulfamoyl]-benzoylamino}-acetic acid (Example 10.1/e) according to the method described in Example 1.1/f.

TABLE 10

| Example | Name | MS (EI) (MH⁺) |
|---|---|---|
| 10.2 | 4-[2-(4-Bromo-2-chloro-phenoxy)-phenylsulfamoyl]-N-{2-oxo-2-[4-(2-pyrrolidin-1-yl-ethyl)-piperazin-1-yl]-ethyl}-benzamide | 705.4 |
| 10.3 | 4-[2-(4-Bromo-2-chloro-phenoxy)-phenylsulfamoyl]-N-{2-oxo-2-[4-(3-pyrrolidin-1-yl-propyl)-piperazin-1-yl]-ethyl}-benzamide | 720.4 |
| 10.4 | 4-[2-(4-Bromo-2-chloro-phenoxy)-phenylsulfamoyl]-N-{2-oxo-2-[4-(2-pyrrolidin-1-yl-ethyl)-piperidin-1-yl]-ethyl}-benzamide | 705.4 |

TABLE 10-continued

| Example | Name | MS (EI) (MH⁺) |
|---|---|---|
| 10.5 | 1-(2-{4-[2-(4-Bromo-2-chloro-phenoxy)-phenylsulfamoyl]-benzoylamino}-acetyl)-piperidine-4-carboxylic acid amide | 651.3 |
| 10.6 | 4-[2-(4-Bromo-2-chloro-phenoxy)-phenylsulfamoyl]-N-[2-(4-hydroxymethyl-piperidin-1-yl)-2-oxo-ethyl]-benzamide | 638.3 |
| 10.7 | 4-[2-(4-Bromo-2-chloro-phenoxy)-phenylsulfamoyl]-N-{2-[4-(1-methyl-piperidin-4-yl)-piperazin-1-yl]-2-oxo-ethyl}-benzamide | 706.4 |

Example 11.1

N-(2-[1,4]-Diazepan-1-yl-2-oxo-ethyl)-4-(2-phenoxy-phenylsulfamoyl)-benzamide hydrochloride To a stirred solution of [4-(2-phenoxy-phenylsulfamoyl)-benzoylamino]-acetic acid (Example 2.1/c) (36 mg, 0.085 mmol) in a mixture of dichloromethane (2 mL) and dimethylformamide (0.2 mL) and [1,4]diazepane-1-carboxylic acid tert-butyl ester (Fluka) (20 mg, 0.1 mmol), HBTU (46 mg, 0.12 mmol) and triethylamine (30 μL, 0.2 mmol) were added. The mixture was stirred at room temperature for 24 h, then purified by column chromatography using Kieselgel 60 (0.015-0.040 mm) as adsorbent (Merck) and gradient elution starting with 100% A eluent and processing to 100% B eluent over a period of 20 minutes (eluent A: n-hexane; eluent B: ethyl acetate). The purified compound was dissolved in ethyl acetate (0.5 mL) 2.5 M hydrogen chloride in ethyl acetate (2.0 mL) was added and the mixture was stirred at room temperature for 24 h. The precipitated product was filtered, washed with diethyl ether and dried in vacuum to yield 29 mg (62%) of the title compound. MS (EI) 509.2 (MH⁺).

Example 11.2

N-(2-Oxo-2-piperazin-1-yl-ethyl)-4-(2-phenoxy-phenylsulfamoyl)-benzamide hyrochloride The title compound was prepared from [4-(2-phenoxy-phenylsulfamoyl)-benzoylamino]-acetic acid (Example 2.1/c) and piperazine-1-carboxylic acid tert-butyl ester (Aldrich) according to the method described in Example 11.1. MS (EI) 495.2 (MH⁺).

Example 11.3

N-[2-(4-Amino-piperidin-1-yl)-2-oxo-ethyl]-4-(2-phenoxy-phenylsulfamoyl)-benzamide hydrochloride The title compound was prepared from [4-(2-phenoxy-phenylsulfamoyl)-benzoylamino]-acetic acid (Example 2.1/c) and piperidin-4-yl-carbamic acid tert-butyl ester (Aldrich) according to the method described in Example 11.1. MS (EI) 509.0 (MH⁺).

Example 11.4

4-[2-(2,4-Dichloro-phenoxy)-phenylsulfamoyl]-N-(2-oxo-2-piperazin-1-yl-ethyl)-benzamide hydrochloride The title compound was prepared from {4-[2-(2,4-dichloro-phenoxy)-phenylsulfamoyl]-benzoylamino}-acetic acid (Example 1.1/e) and piperazine-1-carboxylic acid tert-butyl ester (Aldrich) according to the method described in Example 11.1. MS (EI) 564.2 (MH⁺).

Example 11.5

N-(2-[1,4]Diazepan-1-yl-2-oxo-ethyl)-4-[2-(2,4-dichloro-phenoxy)-phenylsulfamoyl]-benzamide hydrochloride The title compound was prepared from {4-[2-(2,4-dichloro-phenoxy)-phenylsulfamoyl]-benzoylamino}-acetic acid (Example 1.1/e) and [1,4]diazepane-1-carboxylic acid tert-butyl ester (Fluka) according to the method described in Example 11.1. MS (EI) 578.2 (MH⁺).

Example 11.6

4-(2-Benzoyl-phenylsulfamoyl)-N-(2-[1,4]diazepan-1-yl-2-oxo-ethyl)-benzamide hydrochloride The title compound was prepared from [4-(2-benzoyl-phenylsulfamoyl)-benzoylamino]-acetic acid (Example 3.1/c) and [1,4]diazepane-1-carboxylic acid tert-butyl ester (Fluka) according to the method described in Example 11.1. MS (EI) 521.2 (MH⁺).

Example 11.7

4-(2-Benzoyl-phenylsulfamoyl)-N-(2-oxo-2-piperazin-1-yl-ethyl)-benzamide hydrochloride The title compound was prepared from [4-(2-benzoyl-phenylsulfamoyl)-benzoylamino]-acetic acid (Example 3.1/c) and piperazine-1-carboxylic acid tert-butyl ester (Aldrich) according to the method described in Example 11.1. MS (EI) 507.2 (MH⁺).

Example 11.8

N-[2-(4-Amino-piperidin-1-yl)-2-oxo-ethyl]-4-(2-benzoyl-phenylsulfamoyl)-benzamide hydrochloride The title compound was prepared from [4-(2-benzoyl-phenylsulfamoyl)-benzoylamino]-acetic acid (Example 3.1/c) and piperidin-4-yl-carbamic acid tert-butyl ester (Aldrich) according to the method described in Example 11.1. MS (EI) 521.2 (MH⁺).

Example 11.9

N-[2-(4-Amino-piperidin-1-yl)-2-oxo-ethyl]-4-[2-(2,4-dichloro-phenoxy)-phenylsulfamoyl]-benzamide hydrochloride The title compound was prepared from {4-[2-(2,4-dichloro-phenoxy)-phenylsulfamoyl]-benzoylamino}-acetic acid (Example 1.1/e) and piperidin-4-yl-carbamic acid tert-butyl ester (Aldrich) according to the method described in Example 11.1. MS (EI) 577.2 (MH±).

Example 11.10

4-[5-Fluoro-2-(4-fluoro-phenoxy)-phenylsulfamoyl]-N-(2-oxo-2-piperazin-1-yl-ethyl)-benzamide hydrochloride The title compound was prepared from {4-[5-fluoro-2-(4-fluoro-phenoxy)-phenylsulfamoyl]-benzoylamino}-acetic acid (Example 4.1/c) and piperazine-1-carboxylic acid tert-butyl ester (Aldrich) according to the method described in Example 11.1. MS (EI) 531.2 (MH$^+$).

Example 11.11

N-(2-[1,4]Diazepan-1-yl-2-oxo-ethyl)-4-[2-(2,4-dichloro-benzoyl)-phenylsulfamoyl]-benzamide hydrochloride The title compound was prepared from {4-[2-(2,4-dichloro-benzoyl)-phenylsulfamoyl]-benzoylamino}-acetic acid (Example 6.1/c)) and [1,4]diazepane-1-carboxylic acid tert-butyl ester (Fluka) according to the method described in Example 11.1. MS (EI) 589.3 (MH$^+$).

Example 11.12

4-[2-(2,4-Dichloro-benzoyl)-phenylsulfamoyl]-N-(2-oxo-2-piperazin-1-yl-ethyl)-benzamide hydrochloride The title compound was prepared from {4-[2-(2,4-dichloro-benzoyl)-phenylsulfamoyl]-benzoylamino}-acetic acid (Example 6.1/c)) and piperazine-1-carboxylic acid tert-butyl ester (Aldrich) according to the method described in Example 11.1. MS (EI) 575.3 (MH$^+$).

Example 11.13

N-[2-(4-Amino-piperidin-1-yl)-2-oxo-ethyl]-4-[2-(2,4-dichloro-benzoyl)-phenylsulfamoyl]-benzamide hydrochloride The title compound was prepared from {4-[2-(2,4-dichloro-benzoyl)-phenylsulfamoyl]-benzoylamino}-acetic acid (Example 6.1/c)) and piperidin-4-yl-carbamic acid tert-butyl ester (Aldrich) according to the method described in Example 11.1. MS (EI) 589.3 (MH$^+$).

Example 11.14

N-(2-Oxo-2-piperazin-1-yl-ethyl)-4-[2-(4-trifluoromethoxy-phenoxy)-phenylsulfamoyl]-benzamide hydrochloride The title compound was prepared from {4-[2-(4-trifluoromethoxy-phenoxy)-phenylsulfamoyl]-benzoylamino}-acetic acid (Example 9.1/c) and piperazine-1-carboxylic acid tert-butyl ester (Aldrich) according to the method described in Example 11.1. MS (EI) 579.3 (MH$^+$).

Example 11.15

4-[2-(4-Bromo-2-chloro-phenoxy)-phenylsulfamoyl]-N-(2-oxo-2-piperazin-1-yl-ethyl)-benzamide hydrochloride The title compound was prepared from {4-[2-(4-bromo-2-chloro-phenoxy)-phenylsulfamoyl]-benzoylamino}-acetic acid (Example 10.1/e) and piperazine-1-carboxylic acid tert-butyl ester (Aldrich) according to the method described in Example 11.1. MS (EI) 609.2 (MH$^+$).

Example 12

N-((S)-2-2,5-Diaza-bicyclo[2.2.1]hept-2-yl-2-oxo-ethyl)-4-(2-phenoxy-phenylsulfamoyl)-benzamide A stirred mixture of N-[2-((S)-5-benzyl-2,5-diaza-bicyclo [2.2.1]hept-2-yl)-2-oxo-ethyl]-4-(2-phenoxy-phenylsulfamoyl)-benzamide (Example 2.61) (46 mg, 0.077 mmol) and 10% Pd/C (10 mg) in acetic acid (5 mL) was hydrogenated at 5 bar at room temperature for 2 h. The catalyst was filtered off and the filtrate was concentrated in vacuo. The residue was purified by column chromatography using Kieselgel 60 (0.015-0.040 mm) (Merck) as adsorbent and chloroform:methanol:ammonium hydroxide=9:1:0.1 as eluent to yield 37.9 mg (97%) of the title compound. MS (EI) 507.1 (MH$^+$).

Example 13

Preparation of Pharmaceutical Compositions a) Tablets:
0.01-50% of active ingredient of formula (I), 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin were mixed, then granulated by wet granulation and pressed to tablets.

b) Dragées, Filmcoated Tablets:
The tablets made according to the method described above were coated by a layer consisting of entero- or gastrosolvent film, or of sugar and talc. The dragées were polished by a mixture of beeswax and carnuba wax.

c) Capsules:
0.01-50% of active ingredient of formula (I), 1-5% of sodium lauryl sulfate, 15-50% of starch, 15-50% of lactose, 1-3% of colloid silicon dioxide and 0.01-3% of magnesium stearate were thoroughly mixed, the mixture was passed through a sieve and filled in hard gelatin capsules.

d) Suspensions:
Ingredients: 0.01-15% of active ingredient of formula (I), 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To solution of nipagin and citric acid in 20 ml of distilled water, carbopol was added in small portions under vigorous stirring, and the solution was left to stand for 10-12 h. Then the sodium hydroxide in 1 ml of distilled water, the aqueous solution of sorbitol and finally the ethanolic raspberry flavor were added with stirring. To this carrier the active ingredient was added in small portions and suspended with an immersing homogenizer. Finally the suspension was filled up to the desired final volume with distilled water and the suspension syrup was passed through a colloid milling equipment.

e) Suppositories:
For each suppository 0.01-15% of active ingredient of formula (I) and 1-20% of lactose were thoroughly mixed, then 50-95% of adeps pro suppository (for example Witepsol 4) was melted, cooled to 35° C. and the mixture of active ingredient and lactose was mixed in it with homogenizer. The obtained mixture was mould in cooled forms.

f) Lyophilized Powder Ampoule Compositions:
A 5% solution of mannitol or lactose was made with bidistilled water for injection use, and the solution was filtered so as to have sterile solution. A 0.01-5% solution of the active ingredient of formula (I) was also made with bidistilled water for injection use, and this solution was filtered so as to have sterile solution. These two solutions were mixed under aseptic conditions, filled in 1 ml portions into ampoules, the content of the ampoules was lyophilized, and the ampoules were sealed under nitrogen. The contents of the ampoules were dissolved in sterile water or 0.9% (physiological) sterile aqueous sodium chloride solution before administration.

The invention claimed is:

1. A compound of formula (I)

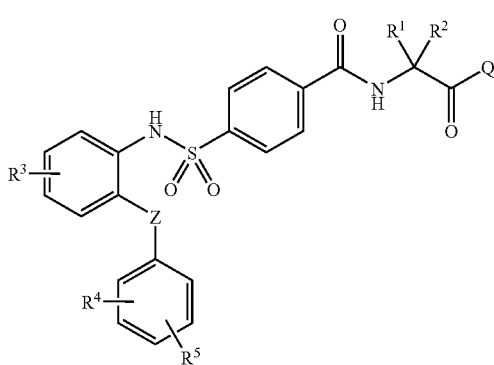

wherein
R$^1$ is selected from a hydrogen atom and C$_1$-C$_4$ alkyl group;
R$^2$ is selected from (1) a hydrogen atom; (2) C$_1$-C$_6$ alkyl group, said C$_1$-C$_6$ alkyl group is straight or branched; (3) —(CH$_2$)$_n$—NH$_2$; (4) —(CH$_2$)$_n$—OH; (5) —(CH$_2$)$_n$—CO—NH$_2$; (6) —(CH$_2$)$_n$—COOR$^e$; and (7) benzyl, said benzyl is optionally substituted with one or more hydroxy group or halogen atom; or
R$^1$, R$^2$ and the carbon atom to which they are both attached together form a 3-7 membered cycloalkyl ring;
R$^3$, R$^4$ and R$^5$ are independently of each other selected from: a hydrogen atom; halogen atom; cyano; nitro; amino; amino substituted with one or more C$_1$-C$_4$ alkyl group;
trifluoromethyl; C$_1$-C$_4$ alkyl; C$_1$-C$_4$ alkoxy; trifluoromethoxy; C$_1$-C$_4$ alkoxycarbonyl; —C(=O)—NH$_2$; and hydroxy group;
Z is selected from (1) single bond; (2) oxygen atom; (3) CH$_2$ group; (4) CO group; (5) NR$^c$ group; (6) S atom; and (7) SO$_2$ group;
Q is selected from

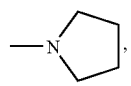

optionally substituted with —(CH$_2$)$_m$—OH group or —(CH$_2$)$_n$—X—P group;

(2)

optionally substituted with one or more C$_1$-C$_4$ alkyl group, one or more halogen atom, —(CH$_2$)$_m$—OH group, —(CH$_2$)$_m$—NH$_2$ group, —(CH$_2$)$_m$—CO—NH$_2$ group, trifluoromethyl group, oxo group, —(CH$_2$)$_m$—CN group, —NH—CO—(C$_1$-C$_4$ alkyl) group, —NH—SO$_2$—(C$_1$-C$_4$ alkyl) group, —(CH$_2$)$_m$—COOR$^e$ group, —CO—NR$^c$R$^d$ group, —(C$_1$-C$_4$ alkoxy) group, —NH—CO—(CH$_2$)$_m$—CF$_3$ group, or —NH—SO$_2$—CH$_2$—CF$_3$ group;

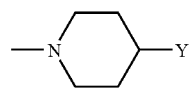

group;

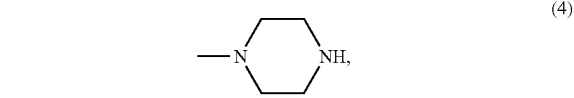

optionally substituted with an oxo group, —SO$_2$—(C$_1$-C$_4$ alkyl) group, C$_1$-C$_4$ alkyl group, —CO—(C$_1$-C$_4$ alkyl) group, —(CH$_2$)$_m$—O—(CH$_2$)$_m$—OH group, —(CH$_2$)$_m$—OH group, —SO$_2$—NR$^c$R$^d$ group, or —CO—NR$^c$R$^d$ group;

group;

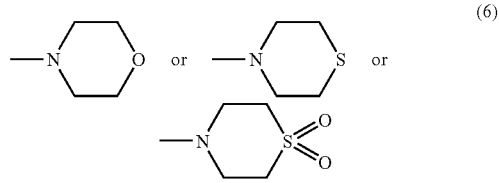

group;

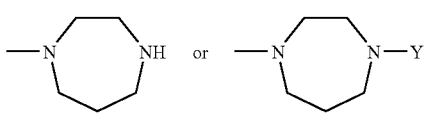

group;

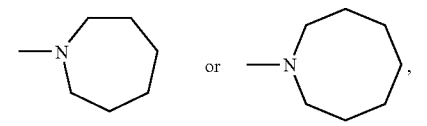

optionally substituted with —(CH$_2$)$_m$—OH group,

group;

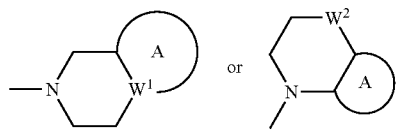

group; and,

group;

Y is selected from (1) —(CH$_2$)$_n$—NR$^a$R$^b$; and, (2) —(CH$_2$)$_n$—X—P group;

n is an integer from 0 to 6;

m is an integer from 0 to 3;

X is selected from (1) single bond; (2) oxygen atom; (3) —CO—NR$^c$ group; (4) CO; and (5) SO$_2$ group;

P is selected from (1) phenyl group, optionally substituted with one or more halogen atom, hydroxy, cyano, amino or C$_1$-C$_4$ alkyl group; (2) a 4-7 membered ring containing 1-3 heteroatom selected from O, S, SO$_2$ and N, said 4-7 membered ring is saturated, partially unsaturated, or aromatic, and said 4-7 membered ring is optionally substituted with one or more halogen atom, oxo, hydroxy, cyano, amino or C$_1$-C$_4$ alkyl group; and, (3) C$_5$-C$_8$ cycloalkyl group;

R$^a$ and R$^b$ are independently of each other selected from (1) hydrogen atom, and (2) C$_1$-C$_6$ alkyl group, said C$_1$-C$_6$ alkyl group is straight or branched, with the proviso that Ra and Rb can not be simultaneously hydrogen atom; or R$^a$, R$^b$ and the nitrogen atom to which they are both attached together form a saturated, partially unsaturated or aromatic 4-7 membered ring containing 0-3 heteroatom (in addition to the nitrogen atom to which R$^a$ and R$^b$ attached) selected from O, S, SO$_2$ and N; wherein said ring is optionally substituted with one or more halogen atom, oxo, cyano, hydroxy or C$_1$-C$_4$ alkyl group;

R$^c$ is selected from a hydrogen atom and C$_1$-C$_4$ alkyl group;

R$^d$ is selected from a hydrogen atom, C$_1$-C$_4$ alkyl group, C$_1$-C$_4$ hydroxyalkyl group, and C$_3$-C$_8$ cycloalkyl group;

R$^e$ is selected from a hydrogen atom, C$_1$-C$_4$ alkyl group, and benzyl group;

A is selected from (1) a C$_4$-C$_7$ cycloalkyl ring; and (2) a 5-7 membered ring containing 0-3 heteroatom selected from O, S, SO$_2$ and N, and wherein said ring is saturated, partially unsaturated or aromatic, and is optionally substituted with one or more halogen atom, oxo, cyano, hydroxy, amino, phenyl or C$_1$-C$_4$ alkyl group;

B is selected from a 4-7 membered ring containing 1-3 heteroatom selected from O, S, SO$_2$ and N; wherein said ring saturated, partially unsaturated or aromatic, and is optionally substituted with one or more halogen atom, oxo, cyano, hydroxy, amino, phenyl or C$_1$-C$_4$ alkyl group;

W$^1$ is selected from a carbon atom, nitrogen atom, and CH group; and,

W$^2$ is selected from an oxygen atom, sulfur atom, NH, CH$_2$ and SO$_2$ group.

2. A compound according to claim 1, wherein the compound is in the form of a pharmaceutically-acceptable salt.

3. A compound according to claim 1, wherein the compound is in the form of a hydrate.

4. A compound according to claim 1, wherein the compound is in the form of a solvate.

5. A compound according to claim 1, wherein the compound is optically active.

6. A racemic mixture of compounds according to claim 5.

7. A compound according to claim 1, wherein the compound is selected from 4-[2-(2,4-dichloro-phenoxy)-phenylsulfamoyl]-N-{2-oxo-2-[4-(2-pyrrolidin-1-yl-ethyl)-piperazin-1-yl]-ethyl}-benzamide; 4-[2-(2,4-dichloro-phenoxy)-phenylsulfamoyl]-N-{2-[4-(2-dimethylamino-ethyl)-piperazin-1-yl]-2-oxo-ethyl}-benzamide; 4-[2-(2,4-dichloro-phenoxy)-phenylsulfamoyl]-N-{2-[4-(2-diethylamino-ethyl)-piperazin-1-yl]-2-oxo-ethyl}-benzamide; 4-[2-(2,4-dichloro-phenoxy)-phenylsulfamoyl]-N-{2-oxo-2-[4-(3-pyrrolidin-1-yl-propyl)-piperazin-1-yl]-ethyl}-benzamide; 4-[2-(2,4-dichloro-phenoxy)-phenylsulfamoyl]-N-{2-[4-(1-methyl-piperidin-3-ylmethyl)-piperazin-1-yl]-2-oxo-ethyl}-benzamide; 4-[2-(2,4-dichloro-phenoxy)-phenylsulfamoyl]-N-{2-oxo-2-[4-(2-pyrrolidin-1-yl-ethyl)-piperidin-1-yl]-ethyl}-benzamide; 4-[2-(2,4-dichloro-phenoxy)-phenylsulfamoyl]-N-[2-oxo-2-(4-pyrimidin-2-yl-piperazin-1-yl)-ethyl]-benzamide; 4-[2-(2,4-dichloro-phenoxy)-phenylsulfamoyl]-N-{2-[4-(3-morpholin-4-yl-propyl)-[1,4]diazepan-1-yl]-2-oxo-ethyl}-benzamide; 4-[2-(2,4-dichloro-phenoxy)-phenylsulfamoyl]-N-{2-oxo-2-[4-(3-piperidin-1-yl-propyl)-piperazin-1-yl]-ethyl}-benzamide; 4-[2-(2,4-dichloro-phenoxy)-phenylsulfamoyl]-N-{2-[4-(3-dimethylamino-propyl)-piperazin-1-yl]-2-oxo-ethyl}-benzamide; 4-[2-(2,4-dichloro-phenoxy)-phenylsulfamoyl]-N-{2-oxo-2-[4-(3-pyrrolidin-1-yl-propyl)-[1,4]diazepan-1-yl]-ethyl}-benzamide; 4-[2-(2,4-dichloro-phenoxy)-phenylsulfamoyl]-N-{2-[4-(3-morpholin-4-yl-propyl)-piperazin-1-yl]-2-oxo-ethyl}-benzamide; 4-[2-(2,4-dichloro-phenoxy)-phenylsulfamoyl]-N-{2-oxo-2-[4-(2-piperidin-1-yl-ethyl)-piperazin-1-yl]-ethyl}-benzamide; 4-[2-(2,4-dichloro-phenoxy)-phenylsulfamoyl]-N-[2-oxo-2-(4-pyrrolidin-1-yl-piperidin-1-yl)-ethyl]-benzamide; 4-[2-(2,4-dichloro-phenoxy)-phenylsulfamoyl]-N-[2-(4-hydroxy-piperidin-1-yl)-2-oxo-ethyl]-benzamide; N-{2-oxo-2-[4-(2-pyrrolidin-1-yl-ethyl)-piperazin-1-yl]-ethyl}-4-(2-phenoxy-phenylsulfamoyl)-benzamide; N-{2-[4-(2-dimethylamino-ethyl)-piperazin-1-yl]-2-oxo-ethyl}-4-(2-phenoxy-phenylsulfamoyl)-benzamide; N-{2-[4-(2-diethylamino-ethyl)-piperazin-1-yl]-2-oxo-ethyl}-4-(2-phenoxy-phenylsulfamoyl)-benzamide; N-{2-oxo-2-[4-(3-pyrrolidin-1-yl-propyl)-piperazin-1-yl]-ethyl}-4-(2-phenoxy-phenylsulfamoyl)-benzamide; N-{2-[4-(3-dimethylamino-propyl)-piperazin-1-yl]-2-oxo-ethyl}-4-(2-phenoxy-phenylsulfamoyl)-benzamide; N-{2-oxo-2-[4-(2-pyrrolidin-1-yl-ethyl)-piperidin-1-yl]-ethyl}-4-(2-phenoxy-phenylsulfamoyl)-benzamide; N-[2-(4-hydroxy-piperidin-1-yl)-2-oxo-ethyl]-4-(2-phenoxy-phenylsulfamoyl)-benzamide; 1-{2-[4-(2-phenoxy-phenylsulfamoyl)-benzoylamino]-acetyl}-piperidine-4-carboxylic acid amide; N-[2-(4-hydroxymethyl-piperidin-1-yl)-2-oxo-ethyl]-4-(2-phenoxy-phenylsulfamoyl)-benzamide; N-{2-[4-(1-methyl-piperidin-4-yl)-piperazin-1-yl]-2-oxo-ethyl}-4-(2-phenoxy-phenylsulfamoyl)-benzamide; N-(2-[1,4]diazepan-1-yl-2- oxo-ethyl)-4-(2-phenoxy-phenylsulfamoyl)-benzamide hydrochloride; N-(2-oxo-2-piperazin-1-yl-ethyl)-4-(2-phenoxy-phenylsulfamoyl)-benzamide hyrochlorid; N-[2-(4-amino-piperidin-1-yl)-2-oxo-ethyl]-4-(2-phenoxy-phenylsulfamoyl)-benzamide hydrochloride; 4-[2-(2,4-dichloro-phenoxy)-phenylsulfamoyl]-N-(2-oxo-2-piperazin-1-yl-ethyl)-benzamide hydrochloride; N-(2-[1,4]diazepan-1-yl-2-oxo-ethyl)-4-[2-(2,4-dichloro-phenoxy)-phenylsulfamoyl]-benzamide hydrochloride; 4-(2-benzoyl-phenylsulfamoyl)-N-{2-oxo-2-[4-(2-pyrrolidin-1-yl-ethyl)-piperazin-1-yl]-ethyl}-benzamide; 4-(2-benzoyl-phenylsulfamoyl)-N-{2-[4-(2-dimethylamino-ethyl)-piperazin-1-yl]-2-oxo-ethyl}-benzamide; 4-(2-benzoyl-phenylsulfamoyl)-N-(2-oxo-2-piperidin-1-yl-ethyl)-benzamide; N-(2-azepan-1-yl-2-oxo-ethyl)-4-(2-benzoyl-phenylsulfamoyl)-benzamide; 4-(2-benzoyl-phenylsulfamoyl)-N-[2-(4-cyano-piperidin-1-yl)-2-oxo-ethyl]-benzamide; 4-(2-benzoyl-phenylsulfamoyl)-N-[2-oxo-2-(4-trifluoromethyl-piperidin-1-yl)-ethyl]-benzamide; 4-(2-benzoyl-phenylsulfamoyl)-N-[2-(4-methyl-piperidin-1-yl)-2-oxo-ethyl]-benzamide; 4-(2-benzoyl-phenylsulfamoyl)-N-{2-[4-(1-methyl-piperidin-3-ylmethyl)-piperazin-1-yl]-2-oxo-ethyl}-benzamide; 4-(2-benzoyl-phenylsulfamoyl)-N-[2-(4-hydroxymethyl-piperidin-1-yl)-2-oxo-ethyl]-benzamide; 4-(2-benzoyl-phenylsulfamoyl)-N-{2-[4-(2-hydroxy-ethyl)-piperidin-1-yl]-2-oxo-ethyl}-benzamide; 4-(2-benzoyl-phenylsulfamoyl)-N-{2-oxo-2-[4-(3-pyrrolidin-1-yl-propyl)-piperazin-1-yl]-ethyl}-benzamide; 4-(2-benzoyl-phenylsulfamoyl)-N-{2-[4-(3-dimethylamino-propyl)-piperazin-1-yl]-2-oxo-ethyl}-benzamide; 4-(2-benzoyl-phenylsulfamoyl)-N-{2-oxo-2-[4-(2-pyrrolidin-1-yl-ethyl)-piperidin-1-yl]-ethyl}-benzamide; 4-(2-benzoyl-phenylsulfamoyl)-N-[2-(4-hydroxy-piperidin-1-yl)-2-oxo-ethyl]-benzamide; 1-{2-[4-(2-benzoyl-phenylsulfamoyl)-benzoylamino]-acetyl}-piperidine-4-carboxylic acid amide; 4-(2-benzoyl-phenylsulfamoyl)-N-(2-[1,4]diazepan-1-yl-2-oxo-ethyl)-benzamide hydrochloride; and, 4-(2-benzoyl-phenylsulfamoyl)-N-(2-oxo-2-piperazin-1-yl-ethyl)-benzamide hydrochloride.

8. A process for preparing a compound of formula (I) in accordance with claim 1, comprising:
(a) reacting an amine derivative of formula (II),

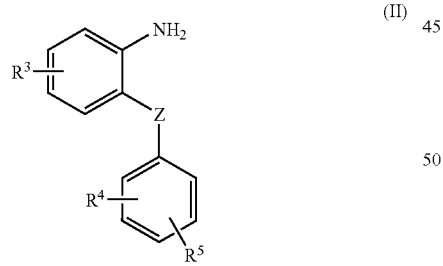

wherein the meaning of $R^3$, $R^4$ and $R^5$ is as described above for the formula (I), with a sulfonyl chloride of formula (III)

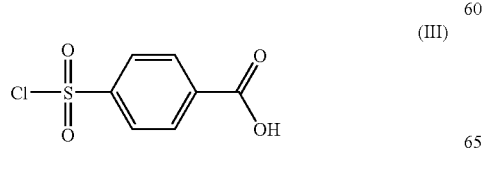

to obtain a compound of formula (IV),

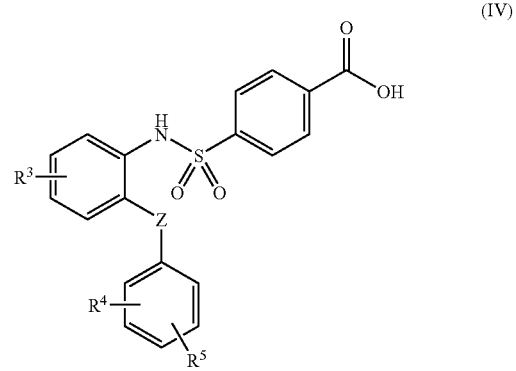

wherein the meaning of $R^3$, $R^4$ and $R^5$ is as described above for the formula (I);
(b) reacting the compound of formula (IV) with an amino acid of formula (V),

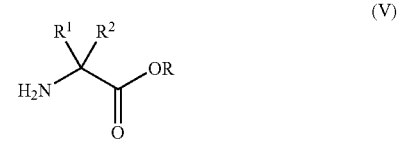

wherein the meaning of $R^1$ and $R^2$ is as described above for the formula (I) and R is $C_1$-$C_4$ alkyl group, to obtain a compound of formula (VI),

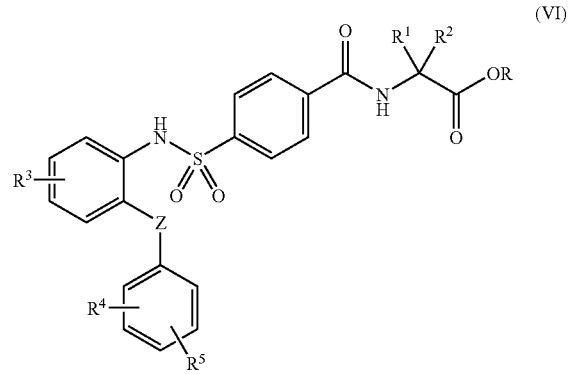

wherein the meaning of $R^1$, $R^2$, $R^3$, $R^4$, $R^5$ and R is as defined above;
(c) hydrolyzing the compound of formula (VI) to furnish an acid derivative of formula (VII),

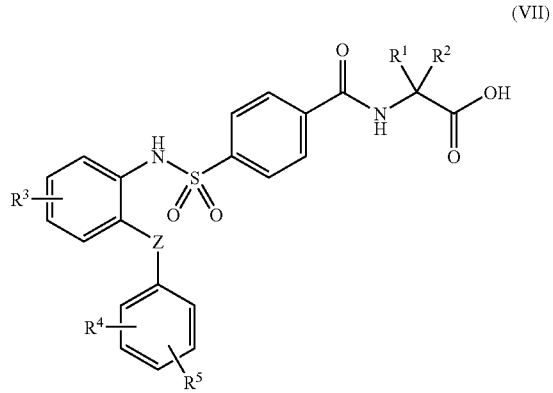

wherein the meaning of $R^1$, $R^2$, $R^3$, $R^4$ and $R^5$ is as defined above; and, (d) reacting the acid derivative of formula (VII) with an amine derivative H-Q, wherein Q is as described in formula (I), resulting in a benzamide derivative of formula (I).

9. A process according to claim 8, wherein the process comprises preparing an optical antipode, racemate, solvate, hydrate, or pharmaceutically-acceptable salt of the phenylsulfamoyl benzamide derivative of formula (I).

10. A process for preparing a compound of formula (I) in accordance with claim 1, comprising transforming a compound of formula (I) into an other compound of formula (I) by one or more of: introducing new substituents; modifying or removing existing substituents; salt formation; or liberating a compound from a salt.

11. A pharmaceutical composition comprising a compound of formula (I) in accordance with claim 1 and one or more pharmaceutically acceptable excipients.

12. A compound of formula (I)

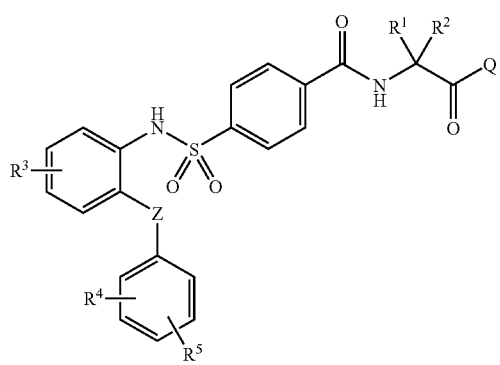

(I)

wherein
$R^1$ is hydrogen atom or $C_1$-$C_4$ alkyl group;
$R^2$ is selected from (1) hydrogen atom; (2) $C_1$-$C_6$ straight or branched alkyl group; (3) —$(CH_2)_n$—$NH_2$; (4) —$(CH_2)_n$—OH; (5) —$(CH_2)_n$—CO—$NH_2$; (6) —$(CH_2)_n$—COOR$^c$ (7) benzyl optionally substituted with one or more hydroxy group or halogen atom; or
$R^1$, $R^2$ and the carbon atom to which they are both attached together form a 3-7 membered cycloalkyl ring;
$R^3$, $R^4$ and $R^5$ are independently of each other hydrogen atom; halogen atom; cyano; nitro; amino; or amino substituted with one or more $C_1$-$C_4$ alkyl group; trifluoromethyl; $C_1$-$C_4$ alkyl; $C_1$-$C_4$ alkoxy; trifluoromethoxy; $C_1$-$C_4$ alkoxycarbonyl; —C(=O)—$NH_2$ or hydroxy group;
Z is selected from (1) single bond; (2) oxygen atom; (3) $CH_2$ group; (4) CO group; (5) NR$^c$ group; (6) S atom; (7) $SO_2$ group;
Q is selected from

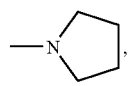

(1)

optionally substituted with —$(CH_2)_m$—OH group, or —$(CH_2)_n$—X—P group;

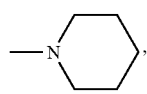

(2)

optionally substituted with one or more $C_1$-$C_4$ alkyl group, one or more halogen atom, —$(CH_2)_m$—OH group, —$(CH_2)_m$—$NH_2$ group, —$(CH_2)_m$—CO—$NH_2$ group, trifluoromethyl group, oxo group; —$(CH_2)_m$—CN group; —NH—CO—($C_1$-$C_4$ alkyl) group, —NH—$SO_2$—($C_1$-$C_4$ alkyl) group, —$(CH_2)_m$—COOR$^c$ group, —CO—NR$^c$R$^d$ group, —($C_1$-$C_4$ alkoxy) group, —NH—CO—$(CH_2)_m$—$CF_3$ group, —NH—$SO_2$—$CH_2$—$CF_3$ group;

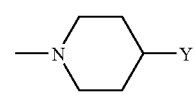

(3)

group;

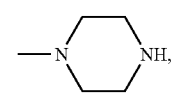

(4)

optionally substituted with oxo group, —$SO_2$—($C_1$-$C_4$ alkyl) group, $C_1$-$C_4$ alkyl group, —CO—($C_1$-$C_4$ alkyl) group, —$(CH_2)_m$—O—$(CH_2)_m$—OH group, —$(CH_2)_m$—OH group, —$SO_2$—NR$^c$R$^d$ group, —CO—NR$^c$R$^d$ group;

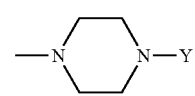

(5)

group;

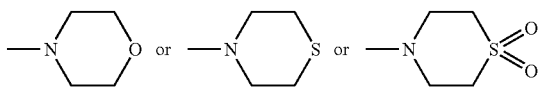

(6)

group;

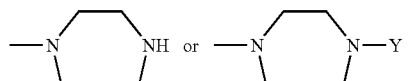

(7)

group;

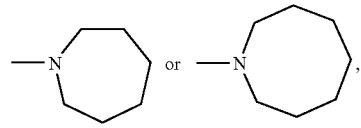

(8)

optionally substituted with —$(CH_2)_m$—OH group,

(9)

group;

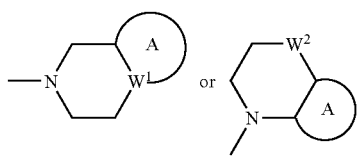

group;

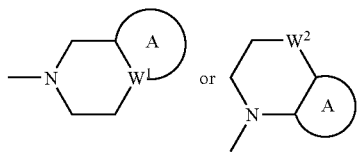

group;
Y is selected from (1) —(CH$_2$)$_n$—NR$^a$R$^b$; (2) —(CH$_2$)$_n$—X—P group;
n is an integer from 0 to 6;
m is an integer from 0 to 3;
X is selected from (1) single bond; (2) oxygen atom; (3) —CO—NR$^c$ group; (4) CO or SO$_2$ group;
P is selected from (1) phenyl group, optionally substituted with one or more halogen atom, hydroxy, cyano, amino or C$_1$-C$_4$ alkyl group; (2) a saturated, partially unsaturated or aromatic 4-7 membered ring containing 1-3 heteroatom selected from O, S, SO$_2$ and N; wherein said ring is optionally substituted with one or more halogen atom, oxo, hydroxy, cyano, amino or C$_1$-C$_4$ alkyl group; (3) C$_5$-C$_8$ cycloalkyl group;
R$^a$ and R$^b$ are (1) hydrogen atom, with the proviso that R$^a$ and R$^b$ can not be simultaneously hydrogen atom; (2) straight or branched C$_1$-C$_6$ alkyl group; (3) R$^a$, R$^b$ and the nitrogen atom to which they are both attached together form a saturated, partially unsaturated or aromatic 4-7 membered ring containing 0-3 heteroatom (in addition to the nitrogen atom to which R$^a$ and R$^b$ attached) selected from O, S, SO$_2$ and N; wherein said ring is optionally substituted with one or more halogen atom, oxo, cyano, hydroxy or C$_1$-C$_4$ alkyl group;
R$^c$ is hydrogen atom or C$_1$-C$_4$ alkyl group;
R$^d$ is hydrogen atom, C$_1$-C$_4$ alkyl group, C$_1$-C$_4$ hydroxyalkyl group, C$_3$-C$_8$ cycloalkyl group;
R$^e$ is hydrogen atom, C$_1$-C$_4$ alkyl group, benzyl group;
A is (1) a C$_4$-C$_7$ cycloalkyl ring; (2) a saturated, partially unsaturated or aromatic 5-7 membered ring containing 0-4 heteroatom including W$^1$ selected from O, S, SO$_2$ and N;
wherein said ring is optionally substituted with one or more halogen atom, oxo, cyano, hydroxy, amino, phenyl or C$_1$-C$_4$ alkyl group;
B is a saturated, partially unsaturated or aromatic 4-7 membered ring containing 1-3 heteroatom selected from O, S, SO$_2$ and N; wherein said ring is optionally substituted with one or more halogen atom, oxo, cyano, hydroxy, amino, phenyl or C$_1$-C$_4$ alkyl group;
W$^1$ is carbon atom, nitrogen atom, or CH group;
W$^2$ is oxygen atom, sulfur atom, NH, CH$_2$ or SO$_2$ group;
or an optical antipode or racemate or pharmaceutically acceptable salt thereof.

13. A compound of claim 12 selected from the group consisting of
4-[2-(2,4-dichloro-phenoxy)-phenylsulfamoyl]-N-{2-oxo-2-[4-(2-pyrrolidin-1-yl-ethyl)-piperazin-1-yl]-ethyl}-benzamide;
4-[2-(2,4-dichloro-phenoxy)-phenylsulfamoyl]-N-{2-[4-(2-dimethylamino-ethyl)-piperazin-1-yl]-2-oxo-ethyl}-benzamide;
4-[2-(2,4-dichloro-phenoxy)-phenylsulfamoyl]-N-{2-[4-(2-diethylamino-ethyl)-piperazin-1-yl]-2-oxo-ethyl}-benzamide;
4-[2-(2,4-dichloro-phenoxy)-phenylsulfamoyl]-N-{2-oxo-2-[4-(3-pyrrolidin-1-yl-propyl)-piperazin-1-yl]-ethyl}-benzamide;
4-[2-(2,4-dichloro-phenoxy)-phenylsulfamoyl]-N-{2-[4-(1-methyl-piperidin-3-ylmethyl)-piperazin-1-yl]-2-oxo-ethyl}-benzamide;
4-[2-(2,4-dichloro-phenoxy)-phenylsulfamoyl]-N-{2-oxo-2-[4-(2-pyrrolidin-1-yl-ethyl)-piperidin-1-yl]-ethyl}-benzamide; 4-[2-(2,4-dichloro-phenoxy)-phenylsulfamoyl]-N-[2-oxo-2-(4-pyrimidin-2-yl-piperazin-1-yl)-ethyl]-benzamide;
4-[2-(2,4-dichloro-phenoxy)-phenylsulfamoyl]-N-{2-[4-(3-morpholin-4-yl-propyl)-[1,4]diazepan-1-yl]-2-oxo-ethyl}-benzamide;
4-[2-(2,4-dichloro-phenoxy)-phenylsulfamoyl]-N-{2-oxo-2-[4-(3-piperidin-1-yl-propyl)-piperazin-1-yl]-ethyl}-benzamide;
4-[2-(2,4-dichloro-phenoxy)-phenylsulfamoyl]-N-{2-[4-(3-dimethylamino-propyl)-piperazin-1-yl]-2-oxo-ethyl}-benzamide;
4-[2-(2,4-dichloro-phenoxy)-phenylsulfamoyl]-N-{2-oxo-2-[4-(3-pyrrolidin-1-yl-propyl)-[1,4]diazepan-1-yl]-ethyl}-benzamide;
4-[2-(2,4-dichloro-phenoxy)-phenylsulfamoyl]-N-{2-[4-(3-morpholin-4-yl-propyl)-piperazin-1-yl]-2-oxo-ethyl}-benzamide;
4-[2-(2,4-dichloro-phenoxy)-phenylsulfamoyl]-N-{2-oxo-2-[4-(2-piperidin-1-yl-ethyl)-piperazin-1-yl]-ethyl}-benzamide;
4-[2-(2,4-dichloro-phenoxy)-phenylsulfamoyl]-N-[2-oxo-2-(4-pyrrolidin-1-yl-piperidin-1-yl)-ethyl]-benzamide;
4-[2-(2,4-dichloro-phenoxy)-phenylsulfamoyl]-N-[2-(4-hydroxy-piperidin-1-yl)-2-oxo-ethyl]-benzamide;
N-{2-[4-(2-dimethylamino-ethyl)-piperazin-1-yl]-2-oxo-ethyl}-4-(2-phenoxy-phenylsulfamoyl)-benzamide;
N-{2-[4-(2-diethylamino-ethyl)-piperazin-1-yl]-2-oxo-ethyl}-4-(2-phenoxy-phenylsulfamoyl)-benzamide;
N-{2-oxo-2-[4-(3-pyrrolidin-1-yl-propyl)-piperazin-1-yl]-ethyl}-4-(2-phenoxy-phenylsulfamoyl)-benzamide;
N-{2-[4-(3-dimethylamino-propyl)-piperazin-1-yl]-2-oxo-ethyl}-4-(2-phenoxy-phenylsulfamoyl)-benzamide;
N-[2-(4-hydroxy-piperidin-1-yl)-2-oxo-ethyl]-4-(2-phenoxy-phenylsulfamoyl)-benzamide;
1-{2-[4-(2-phenoxy-phenylsulfamoyl)-benzoylamino]-acetyl}-piperidine-4-carboxylic acid amide;
N-[2-(4-hydroxymethyl-piperidin-1-yl)-2-oxo-ethyl]-4-(2-phenoxy-phenylsulfamoyl)-benzamide;
N-{2-[4-(1-methyl-piperidin-4-yl)-piperazin-1-yl]-2-oxo-ethyl}-4-(2-phenoxy-phenylsulfamoyl)-benzamide;
N-(2-[1,4]diazepan-1-yl-2-oxo-ethyl)-4-(2-phenoxy-phenylsulfamoyl)-benzamide hydrochloride;
N-(2-oxo-2-piperazin-1-yl-ethyl)-4-(2-phenoxy-phenylsulfamoyl)-benzamide hyrochlorid;

N-[2-(4-amino-piperidin-1-yl)-2-oxo-ethyl]-4-(2-phenoxy-phenylsulfamoyl)-benzamide hydrochloride;
4-[2-(2,4-dichloro-phenoxy)-phenylsulfamoyl]-N-(2-oxo-2-piperazin-1-yl-ethyl)-benzamide hydrochloride;
N-(2-[1,4]diazepan-1-yl-2-oxo-ethyl)-4-[2-(2,4-dichlorophenoxy)-phenylsulfamoyl]-benzamide hydrochloride;
4-(2-benzoyl-phenylsulfamoyl)-N-{2-oxo-2-[4-(2-pyrrolidin-1-yl-ethyl)-piperazin-1-yl]-ethyl}-benzamide;
4-(2-benzoyl-phenylsulfamoyl)-N-{2-[4-(2-dimethylamino-ethyl)-piperazin-1-yl]-2-oxo-ethyl}-benzamide;
4-(2-benzoyl-phenylsulfamoyl)-N-(2-oxo-2-piperidin-1-yl-ethyl)-benzamide;
N-(2-azepan-1-yl-2-oxo-ethyl)-4-(2-benzoyl-phenylsulfamoyl)-benzamide;
4-(2-benzoyl-phenylsulfamoyl)-N-[2-(4-cyano-piperidin-1-yl)-2-oxo-ethyl]-benzamide;
4-(2-benzoyl-phenylsulfamoyl)-N-[2-oxo-2-(4-trifluoromethyl-piperidin-1-yl)-ethyl]-benzamide;
4-(2-benzoyl-phenylsulfamoyl)-N-[2-(4-methyl-piperidin-1-yl)-2-oxo-ethyl]-benzamide;
4-(2-benzoyl-phenylsulfamoyl)-N-{2-[4-(1-methyl-piperidin-3-ylmethyl)-piperazin-1-yl]-2-oxo-ethyl}-benzamide;
4-(2-benzoyl-phenylsulfamoyl)-N-[2-(4-hydroxymethyl-piperidin-1-yl)-2-oxo-ethyl]-benzamide;
4-(2-benzoyl-phenylsulfamoyl)-N-{2-[4-(2-hydroxy-ethyl)-piperidin-1-yl]-2-oxo-ethyl}-benzamide;
4-(2-benzoyl-phenylsulfamoyl)-N-{2-oxo-2-[4-(3-pyrrolidin-1-yl-propyl)-piperazin-1-yl]-ethyl}-benzamide;
4-(2-benzoyl-phenylsulfamoyl)-N-{2-[4-(3-dimethylamino-propyl)-piperazin-1-yl]-2-oxo-ethyl}-benzamide;
4-(2-benzoyl-phenylsulfamoyl)-N-[2-(4-hydroxy-piperidin-1-yl)-2-oxo-ethyl]-benzamide;
1-{2-[4-(2-benzoyl-phenylsulfamoyl)-benzoylamino]-acetyl}-piperidine-4-carboxylic acid amide;
4-(2-benzoyl-phenylsulfamoyl)-N-(2-[1,4]diazepan-1-yl-2-oxo-ethyl)-benzamide hydrochloride;
4-(2-benzoyl-phenylsulfamoyl)-N-(2-oxo-2-piperazin-1-yl-ethyl)-benzamide hydrochloride.

14. A compound of claim 1 selected from the group consisting of
N-{2-oxo-2-[4-(2-pyrrolidin-1-yl-ethyl)-piperazin-1-yl]-ethyl}-4-(2-phenoxy-phenylsulfamoyl)-benzamide;
N-{2-oxo-2-[4-(2-pyrrolidin-1-yl-ethyl)-piperidin-1-yl]-ethyl}-4-(2-phenoxy-phenylsulfamoyl)-benzamide;
4-(2-benzoyl-phenylsulfamoyl)-N-{2-oxo-2-[4-(2-pyrrolidin-1-yl-ethyl)-piperidin-1-yl]-ethyl}-benzamide;
4-[5-fluoro-2-(4-fluoro-phenoxy)-phenylsulfamoyl]-N-{2-oxo-2-[4-(2-pyrrolidin-1-yl-ethyl)-piperidin-1-yl]-ethyl}-benzamide;
4-[2-(4-fluoro-phenoxy)-phenylsulfamoyl]-N-[2-(4-hydroxy-piperidin-1-yl)-2-oxo-ethyl]-benzamide.

* * * * *

UNITED STATES PATENT AND TRADEMARK OFFICE
CERTIFICATE OF CORRECTION

PATENT NO. : 8,481,527 B2
APPLICATION NO. : 12/447157
DATED : July 9, 2013
INVENTOR(S) : Istvan Vago et al.

It is certified that error appears in the above-identified patent and that said Letters Patent is hereby corrected as shown below:

On the Title Page, Item (56)

Page 2, Column 1, line 13 (Other Publications), please delete "bradykin" and insert --bradykinin--, therefor;

Page 2, Column 1, line 21 (Other Publications), please delete "neurones" and insert --neurons--, therefor;

Page 2, Column 1, line 24 (Other Publications), please delete "2- trifluoromethoxydibenz" and insert --2-trifluoromethoxydibenz--, therefor;

Page 2, Column 1, line 46 (Other Publications), please delete "1woth806." and insert --1806.--, therefor;

Page 2, Column 2, line 21 (Other Publications), please delete "Bl" and insert --B1--, therefor;

Page 2, Column 2, line 59 (Other Publications), please delete "Bl" and insert --B1--, therefor;

Page 3, Column 1, line 12 (Other Publications), please delete "sulfony1 ]" and insert --sulfonyl]--, therefor;

Page 3, Column 1, line 13 (Other Publications), please delete "methy1]" and insert --methyl]--, therefor;

Page 3, Column 1, line 27 (Other Publications), please delete "ameloriates" and insert --ameliorates--, therefor;

Page 3, Column 1, line 36 (Other Publications), please delete "streptozotocininduced" and insert --streptozotocin induced--, therefor;

Signed and Sealed this
Eighth Day of July, 2014

Michelle K. Lee
*Deputy Director of the United States Patent and Trademark Office*

CERTIFICATE OF CORRECTION (continued)
U.S. Pat. No. 8,481,527 B2

Page 3, Column 2, line 10 (Other Publications), please delete "streptozotocindiabetic" and insert --streptozotocin diabetic--, therefor;

Page 3, Column 2, lines 16-17 (Other Publications), please delete "6-d imethylphenyl)" and insert --6-dimethylphenyl)--, therefor;

Page 3, Column 2, line 26 (Other Publications), please delete "bradykininmediated" and insert --bradykinin mediated--, therefor;

Page 3, Column 2, line 57 (Other Publications), please delete "421-250" and insert --421:250--, therefor;

Page 4, Column 2, line 1 (Other Publications), please delete "imadazolidines" and insert --imidazolines--, therefor;

In the Claims

Column 43, line 47 (Claim 1), please delete "Ra and Rb" and insert --$R^a$ and $R^b$--, therefor;

Column 43, line 52 (Claim 1), please insert the word --are-- before "attached", therefor;

Column 43, line 67 (Claim 1), please insert the word --is-- before "saturated", therefor;

Column 45, line 3 (Claim 7), please delete "hyrochlorid;" and insert --hydrochloride;--, therefor;

Column 47, line 42 (Claim 12), please insert --; and-- before "(7)", therefor;

Column 47, line 52 (Claim 12), please insert --and-- before "(7)", therefor;

Column 48, line 7 (Claim 12), please insert --or-- before "—NH—", therefor;

Column 48, line 26 (Claim 12), please insert --or-- before "—CO—", therefor;

Column 49, lines 15-20 (Claim 12), please delete

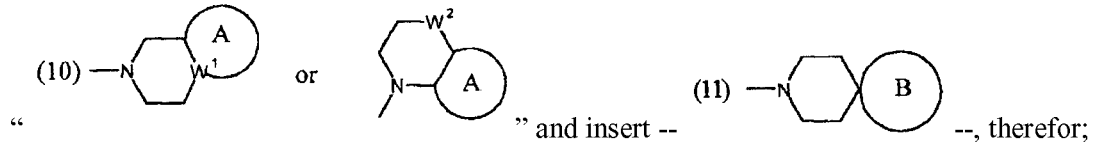

Column 49, line 24 (Claim 12), please insert --and-- before "(2)", therefor;

Column 49, line 29 (Claim 12), please delete "or" and insert --and-- before "$SO_2$", therefor;

Column 49, line 37 (Claim 12), please insert --and-- before "(3)", therefor;

CERTIFICATE OF CORRECTION (continued)
U.S. Pat. No. 8,481,527 B2

Column 49, line 40 (Claim 12), please insert --or-- before "(3)", therefor;

Column 49, line 45 (Claim 12), please insert --are-- before "attached", therefor;

Column 49, line 50 (Claim 12), please insert --or-- before "$C_3$", therefor;

Column 49, line 51 (Claim 12), please insert --or-- before "benzyl", therefor;

Column 49, line 52 (Claim 12), please insert --and-- before "(2)", therefor;

Column 50, line 67 (Claim 13), please delete "hyrochlorid;" and insert --hydrochloride;--, therefor.

UNITED STATES PATENT AND TRADEMARK OFFICE
CERTIFICATE OF CORRECTION

PATENT NO. : 8,481,527 B2
APPLICATION NO. : 12/447157
DATED : July 9, 2013
INVENTOR(S) : Vago et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Tenth Day of February, 2015

Michelle K. Lee
*Deputy Director of the United States Patent and Trademark Office*